(12) United States Patent
Hatzidakis et al.

(10) Patent No.: US 12,220,319 B2
(45) Date of Patent: Feb. 11, 2025

(54) SHOULDER ARTHROPLASTY IMPLANT SYSTEM

(71) Applicant: Integrated Shoulder Collaboration, Inc., Plainsboro, NJ (US)

(72) Inventors: Armodios M. Hatzidakis, Denver, CO (US); Heinz R. Hoenecke, Jr., Del Mar, CA (US); Scott R. Jacobson, Bend, OR (US); James D. Kelly, II, San Francisco, CA (US); Drew Miller, Atlanta, GA (US); Darryl D'Lima, San Diego, CA (US); Nathaniel E. Skinner, Salt Lake City, UT (US)

(73) Assignee: Integrated Shoulder Collaboration, Inc., Plainsboro, NJ (US)

( * ) Notice: Subject to any disclaimer, the term of this patent is extended or adjusted under 35 U.S.C. 154(b) by 449 days.

(21) Appl. No.: 17/228,377

(22) Filed: Apr. 12, 2021

(65) Prior Publication Data
US 2021/0228368 A1    Jul. 29, 2021

Related U.S. Application Data

(63) Continuation of application No. 16/208,324, filed on Dec. 3, 2018, now Pat. No. 11,033,399, which is a
(Continued)

(51) Int. Cl.
*A61F 2/40* (2006.01)
*A61B 17/16* (2006.01)
(Continued)

(52) U.S. Cl.
CPC ............ *A61F 2/40* (2013.01); *A61B 17/1659* (2013.01); *A61B 17/1684* (2013.01);
(Continued)

(58) Field of Classification Search
CPC ........ A61F 2/40; A61F 2/4014; A61F 2/4003; A61F 2/4059
See application file for complete search history.

(56) References Cited

U.S. PATENT DOCUMENTS

| | | | |
|---|---|---|---|
| 4,986,833 | A | 1/1991 | Worland |
| 5,032,132 | A | 7/1991 | Matsen, III et al. |

(Continued)

FOREIGN PATENT DOCUMENTS

| | | |
|---|---|---|
| EP | 1598034 B1 | 3/2011 |
| EP | 2586387 A1 | 5/2013 |

(Continued)

OTHER PUBLICATIONS

International search report with written opinion dated May 24, 2017 for PCT/US2017/020027.
(Continued)

*Primary Examiner* — Brian A Dukert
(74) *Attorney, Agent, or Firm* — KDW Firm PLLC

(57) ABSTRACT

An implant for shoulder arthroplasty includes a stem and optionally a head component or a cup component. The stem is sized and shaped to fit into an intramedullary canal of the humerus. The proximal portion of the stem has a concave taper and the distal portion of the stem has a taper. The distal taper includes an anterior-posterior taper and a medial-lateral taper. The shape of the stem loads the metaphysis of the humerus with a greater load than the load applied to the diaphysis of the humerus.

13 Claims, 32 Drawing Sheets

Related U.S. Application Data continuation of application No. 15/445,658, filed on Feb. 28, 2017, now Pat. No. 10,172,714.

(60) Provisional application No. 62/300,853, filed on Feb. 28, 2016.

(51) Int. Cl.
*A61B 17/17* (2006.01)
*A61B 17/68* (2006.01)
*A61F 2/28* (2006.01)
*A61F 2/30* (2006.01)
*A61F 2/46* (2006.01)

(52) U.S. Cl.
CPC .......... *A61B 17/1778* (2016.11); *A61B 17/68* (2013.01); *A61F 2/28* (2013.01); *A61F 2/30* (2013.01); *A61F 2/4003* (2013.01); *A61F 2/4059* (2013.01); *A61F 2002/2835* (2013.01); *A61F 2002/30331* (2013.01); *A61F 2002/30332* (2013.01); *A61F 2002/305* (2013.01); *A61F 2002/30841* (2013.01); *A61F 2002/30884* (2013.01); *A61F 2002/4022* (2013.01); *A61F 2/4612* (2013.01)

(56) References Cited

U.S. PATENT DOCUMENTS

| | | | |
|---|---|---|---|
| 5,658,348 A | 8/1997 | Rohr, Jr. |
| 5,728,161 A | 3/1998 | Camino et al. |
| 6,283,999 B1 | 9/2001 | Rockwood, Jr. |
| 6,364,910 B1 | 4/2002 | Shultz et al. |
| 6,368,353 B1 | 4/2002 | Arcand |
| 6,406,495 B1 | 6/2002 | Schoch |
| 6,558,425 B2 | 5/2003 | Rockwood et al. |
| 6,652,591 B2 | 11/2003 | Serbousek et al. |
| 6,673,115 B2 | 1/2004 | Resch et al. |
| 6,699,289 B2 | 3/2004 | Iannotti et al. |
| 6,733,502 B2 | 5/2004 | Altarac et al. |
| 6,761,740 B2 | 7/2004 | Tornier |
| 6,790,234 B1 | 9/2004 | Frankle |
| 6,887,277 B2 | 5/2005 | Rauscher et al. |
| 6,899,736 B1 | 5/2005 | Rauscher et al. |
| 6,911,047 B2 | 6/2005 | Rockwood, Jr. et al. |
| 6,942,699 B2 | 9/2005 | Stone et al. |
| 6,953,478 B2 | 10/2005 | Bouttens et al. |
| 6,955,677 B2 | 10/2005 | Dahners |
| 6,969,406 B2 | 11/2005 | Tornier |
| 7,001,389 B1 | 2/2006 | Navarro et al. |
| 7,011,686 B2 | 3/2006 | Ball et al. |
| 7,160,328 B2 | 1/2007 | Rockwood, Jr. et al. |
| 7,169,184 B2 | 1/2007 | Dalla Pria |
| 7,175,663 B1 | 2/2007 | Stone |
| 7,204,854 B2 | 4/2007 | Guederian et al. |
| 7,241,314 B1 | 7/2007 | Winslow |
| 7,309,360 B2 | 12/2007 | Tornier et al. |
| 7,329,284 B2 | 2/2008 | Maroney et al. |
| 7,338,528 B2 | 3/2008 | Stone et al. |
| 7,445,638 B2 | 11/2008 | Beguin et al. |
| 7,462,197 B2 | 12/2008 | Tornier et al. |
| 7,476,253 B1 | 1/2009 | Craig et al. |
| 7,556,652 B2 | 7/2009 | Angibaud et al. |
| 7,604,665 B2 | 10/2009 | Iannotti et al. |
| 7,611,539 B2 | 11/2009 | Bouttens et al. |
| 7,621,961 B2 | 11/2009 | Stone |
| 7,637,928 B2 | 12/2009 | Fernandez |
| 7,753,959 B2 | 7/2010 | Berelsman et al. |
| 7,819,923 B2 | 10/2010 | Stone et al. |
| 7,854,768 B2 | 12/2010 | Wiley et al. |
| 7,892,287 B2 | 2/2011 | Deffenbaugh |
| 7,918,895 B2 | 4/2011 | Isch et al. |
| 7,922,769 B2 | 4/2011 | Deffenbaugh et al. |
| 7,947,135 B2 | 5/2011 | Fonte |
| 8,048,161 B2 | 11/2011 | Guederian et al. |
| 8,062,294 B2 | 11/2011 | Reynolds |
| 8,062,376 B2 | 11/2011 | Shultz et al. |
| 8,070,820 B2 | 12/2011 | Winslow et al. |
| 8,080,063 B2 | 12/2011 | Ferrand et al. |
| 8,092,466 B2 | 1/2012 | Splieth et al. |
| 8,123,815 B2 | 2/2012 | Meridew et al. |
| 8,231,683 B2 | 7/2012 | Lappin et al. |
| 8,236,059 B2 | 8/2012 | Stone et al. |
| 8,241,366 B2 | 8/2012 | Roche et al. |
| 8,246,687 B2 | 8/2012 | Katrana et al. |
| 8,323,347 B2 | 12/2012 | Guederian et al. |
| 8,337,563 B2 | 12/2012 | Roche et al. |
| 8,382,807 B2 | 2/2013 | Austin et al. |
| 8,425,614 B2 | 4/2013 | Winslow et al. |
| 8,444,698 B2 | 5/2013 | Klotz et al. |
| 8,454,702 B2 | 6/2013 | Smits et al. |
| 8,465,548 B2 | 6/2013 | Long |
| 8,480,750 B2 | 7/2013 | Long |
| 8,486,116 B2 | 7/2013 | Heilman |
| 8,500,784 B2 | 8/2013 | Hulliger et al. |
| 8,512,410 B2 | 8/2013 | Metcalfe et al. |
| 8,556,980 B2 | 10/2013 | Deffenbaugh |
| 8,562,686 B2 | 10/2013 | Klotz et al. |
| 8,574,268 B2 | 11/2013 | Chan et al. |
| 8,663,335 B2 | 3/2014 | Katrana et al. |
| 8,690,951 B2 | 4/2014 | Baum et al. |
| 8,690,952 B2 | 4/2014 | Dallmann |
| 8,721,726 B2 | 5/2014 | Capon et al. |
| 8,721,727 B2 | 5/2014 | Ratron et al. |
| 8,721,728 B2 | 5/2014 | Winslow et al. |
| 8,728,129 B2 | 5/2014 | Fritzinger et al. |
| 8,764,836 B2 | 7/2014 | De Wilde et al. |
| 8,795,379 B2 | 8/2014 | Smith et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,907 B2 | 11/2014 | Baptista et al. |
| 8,882,845 B2 | 11/2014 | Wirth et al. |
| 8,906,103 B2 | 12/2014 | Stone et al. |
| 8,940,054 B2 | 1/2015 | Wiley et al. |
| 8,945,234 B2 | 2/2015 | Humphrey |
| 8,968,410 B2 | 3/2015 | Veronesi et al. |
| 8,974,536 B2 | 3/2015 | Walch et al. |
| 8,992,623 B2 | 3/2015 | Hopkins et al. |
| 9,039,745 B2 | 5/2015 | Fritzinger |
| 9,044,330 B2 | 6/2015 | Chavarria et al. |
| 9,066,806 B2 | 6/2015 | Phipps |
| 9,072,554 B2 | 7/2015 | Reynolds et al. |
| 9,084,680 B2 | 7/2015 | Katrana et al. |
| 9,089,435 B2 | 7/2015 | Walch et al. |
| 9,132,012 B2 | 9/2015 | Klotz et al. |
| 9,161,843 B2 | 10/2015 | Anthony et al. |
| 9,226,830 B2 | 1/2016 | De Wilde et al. |
| 9,233,003 B2 | 1/2016 | Roche et al. |
| 9,241,803 B2 | 1/2016 | Stone et al. |
| 9,259,255 B2 | 2/2016 | Lewis et al. |
| 9,278,005 B2 | 3/2016 | Smits et al. |
| 9,283,075 B2 | 3/2016 | Wiley et al. |
| 9,283,083 B2 | 3/2016 | Winslow et al. |
| 9,301,848 B2 | 4/2016 | Long |
| 9,320,619 B2 | 4/2016 | Anthony et al. |
| 9,351,844 B2 | 5/2016 | Walch et al. |
| 9,358,119 B2 | 6/2016 | Ratron et al. |
| 9,387,022 B2 | 7/2016 | Koay et al. |
| 9,402,730 B2 | 8/2016 | Lederman et al. |
| 9,433,507 B2 | 9/2016 | Reubelt et al. |
| 9,433,508 B2 | 9/2016 | Phipps |
| 9,439,769 B2 | 9/2016 | Wirth et al. |
| 9,474,619 B2 | 10/2016 | Reubelt et al. |
| 9,480,570 B2 | 11/2016 | Winslow |
| 9,498,334 B2 | 11/2016 | Lappin et al. |
| 9,498,344 B2 | 11/2016 | Hodorek et al. |
| 9,498,345 B2 | 11/2016 | Burkhead, Jr. et al. |
| 9,510,951 B2 | 12/2016 | Bachmaier et al. |
| 9,522,067 B2 | 12/2016 | Frankle et al. |
| 9,526,549 B2 | 12/2016 | Beyar et al. |
| 9,545,311 B2 | 1/2017 | Courtney, Jr. et al. |
| 9,549,820 B2 | 1/2017 | Mroczkowski et al. |

(56) References Cited

U.S. PATENT DOCUMENTS

| | | |
|---|---|---|
| 9,554,837 B2 | 1/2017 | Schonhardt et al. |
| 9,585,769 B2 | 3/2017 | Lubensky et al. |
| 9,597,203 B2 | 3/2017 | Emerick et al. |
| 9,603,712 B2 | 3/2017 | Bachmaier |
| 9,610,165 B2 | 4/2017 | Poncet et al. |
| 9,622,869 B2 | 4/2017 | Nerot et al. |
| 9,636,237 B2 | 5/2017 | Anthony et al. |
| 9,642,710 B2 | 5/2017 | Winslow et al. |
| 9,687,282 B2 | 6/2017 | Strnad et al. |
| 9,693,880 B2 | 7/2017 | Anthony et al. |
| 9,700,422 B2 | 7/2017 | Katrana et al. |
| 9,700,423 B2 | 7/2017 | Stone et al. |
| 9,700,436 B2 | 7/2017 | Anthony et al. |
| 9,700,437 B2 | 7/2017 | Anthony et al. |
| 9,713,533 B2 | 7/2017 | Taylor et al. |
| 9,713,540 B2 | 7/2017 | Anthony et al. |
| 9,763,798 B2 | 9/2017 | Chavarria et al. |
| 9,763,799 B2 | 9/2017 | Smits et al. |
| 9,770,334 B2 | 9/2017 | Wiley et al. |
| 9,788,874 B2 | 10/2017 | Clasbrummel et al. |
| 9,814,471 B2 | 11/2017 | Goldberg et al. |
| 9,814,588 B2 | 11/2017 | Goldberg |
| 9,833,327 B2 | 12/2017 | Basamania et al. |
| 9,925,047 B2 | 3/2018 | Klotz et al. |
| 9,943,419 B2 | 4/2018 | Anthony et al. |
| 10,028,838 B2 | 7/2018 | Hodorek et al. |
| 10,034,759 B2 | 7/2018 | Deransart et al. |
| 10,034,777 B2 | 7/2018 | Poncet et al. |
| 10,064,734 B2 | 9/2018 | Burkhead, Jr. et al. |
| 10,085,856 B2 | 10/2018 | Anthony et al. |
| 10,143,558 B2 | 12/2018 | Frankle |
| 10,172,714 B2 | 1/2019 | Hatzidakis et al. |
| 10,251,755 B2 | 4/2019 | Boileau et al. |
| 10,335,285 B2 | 7/2019 | Viscardi et al. |
| 10,383,735 B2 | 8/2019 | Wiley et al. |
| 10,413,416 B2 | 9/2019 | Boileau et al. |
| 10,433,967 B2 | 10/2019 | Deransart et al. |
| 10,456,264 B2 | 10/2019 | Hodorek et al. |
| 10,463,499 B2 | 11/2019 | Emerick et al. |
| 10,517,736 B2 | 12/2019 | Lappin et al. |
| 10,524,922 B2 | 1/2020 | Courtney, Jr. et al. |
| 10,524,931 B2 | 1/2020 | Lubensky et al. |
| 10,548,737 B2 | 2/2020 | Hodorek et al. |
| 10,561,501 B2 | 2/2020 | Axelson, Jr. et al. |
| 10,603,181 B2 | 3/2020 | Stone et al. |
| 10,631,993 B2 | 4/2020 | Walch et al. |
| 10,632,000 B2 | 4/2020 | Anthony et al. |
| 10,687,951 B2 | 6/2020 | Basamania et al. |
| 10,702,390 B2 | 7/2020 | Chavarria et al. |
| 10,722,373 B2 | 7/2020 | Hodorek et al. |
| 2002/0177900 A1 | 11/2002 | Serbousek et al. |
| 2003/0171821 A1 | 9/2003 | Draenert et al. |
| 2006/0069445 A1 | 3/2006 | Ondrla et al. |
| 2007/0173945 A1* | 7/2007 | Wiley ............... A61F 2/30734 |
| | | 623/19.13 |
| 2007/0219638 A1 | 9/2007 | Jones et al. |
| 2008/0234833 A1 | 9/2008 | Bandoh et al. |
| 2009/0248087 A1 | 10/2009 | Lewis et al. |
| 2010/0312286 A1 | 12/2010 | Dell'Oca |
| 2011/0029089 A1 | 2/2011 | Giuliani et al. |
| 2011/0060417 A1 | 3/2011 | Simmen et al. |
| 2011/0118795 A1 | 5/2011 | Hashmi et al. |
| 2011/0202092 A1 | 8/2011 | Frigg et al. |
| 2012/0172996 A1* | 7/2012 | Ries ................... A61F 2/3672 |
| | | 623/23.44 |
| 2012/0209392 A1 | 8/2012 | Angibaud et al. |
| 2012/0323284 A1 | 12/2012 | Baker et al. |
| 2014/0236304 A1* | 8/2014 | Hodorek .............. A61F 2/4612 |
| | | 623/19.14 |
| 2014/0277181 A1 | 9/2014 | Garlock |
| 2014/0379089 A1 | 12/2014 | Bachmaier et al. |
| 2015/0134066 A1 | 5/2015 | Bachmaier et al. |
| 2015/0250601 A1 | 9/2015 | Humphrey |
| 2015/0265411 A1 | 9/2015 | Deransart et al. |
| 2015/0359575 A1 | 12/2015 | Pech et al. |
| 2016/0262902 A1 | 9/2016 | Winslow et al. |
| 2016/0270922 A1 | 9/2016 | Pressacco et al. |
| 2016/0374815 A1 | 12/2016 | Siccardi et al. |
| 2017/0049573 A1 | 2/2017 | Hodorek et al. |
| 2017/0319248 A1 | 11/2017 | Milella, Jr. et al. |
| 2017/0340449 A1 | 11/2017 | Deransart et al. |
| 2017/0367836 A1 | 12/2017 | Cardon et al. |
| 2018/0000598 A1* | 1/2018 | Amis ................... A61F 2/3672 |
| 2018/0064537 A1 | 3/2018 | Pressacco et al. |
| 2018/0092747 A1 | 4/2018 | Hopkins |
| 2018/0104065 A1 | 4/2018 | Amis et al. |
| 2018/0193074 A1 | 7/2018 | Hopkins |
| 2018/0193150 A1 | 7/2018 | Winslow et al. |
| 2018/0200067 A1 | 7/2018 | Axelson, Jr. et al. |
| 2018/0303619 A1 | 10/2018 | Kehres et al. |
| 2018/0318096 A1 | 11/2018 | Boulris |
| 2019/0076261 A1 | 3/2019 | Mutchler et al. |

FOREIGN PATENT DOCUMENTS

| | | |
|---|---|---|
| EP | 2604224 A1 | 6/2013 |
| EP | 2604225 A1 | 6/2013 |
| EP | 2604226 A1 | 6/2013 |
| EP | 2773290 A1 | 9/2014 |
| EP | 2083759 B1 | 9/2015 |
| EP | 2689750 B1 | 8/2016 |
| FR | 2737107 B1 | 9/1997 |
| FR | 2652498 B1 | 12/1997 |
| FR | 2848099 B1 | 2/2005 |
| JP | 2015093202 A | 5/2015 |
| WO | WO-0167988 A2 | 9/2001 |
| WO | WO-0217822 A1 | 3/2002 |
| WO | WO-2013064569 A1 | 5/2013 |
| WO | WO-2016094739 A1 | 6/2016 |
| WO | 2017147618 A1 | 8/2017 |
| WO | WO-2017184792 A1 | 10/2017 |

OTHER PUBLICATIONS

Orthoinfo; "Shoulder Joint Replacement"; web page Dec. 12, 2015. [https://web.archive.org/web/20151221081244/http://orthoinfo.aaos.org/topic.cfm?topic=A00094; downloaded from World Wide Web May 2, 2017].

U.S. Appl. No. 15/445,658 Office Action dated May 15, 2018.

Extended European Search Report dated Jun. 19, 2020 for EP17757446.

* cited by examiner

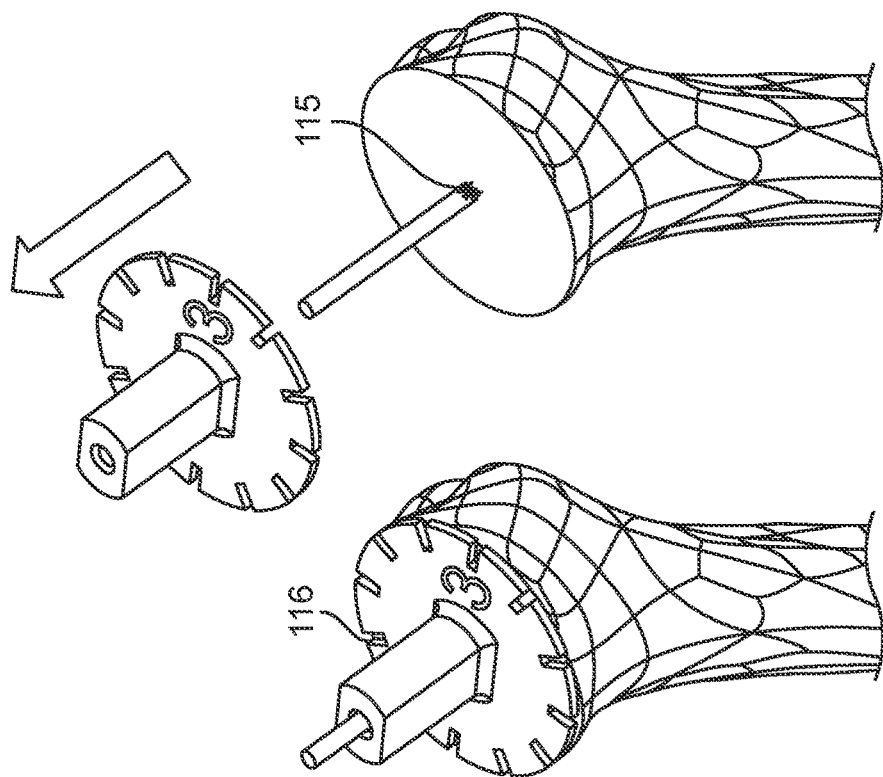
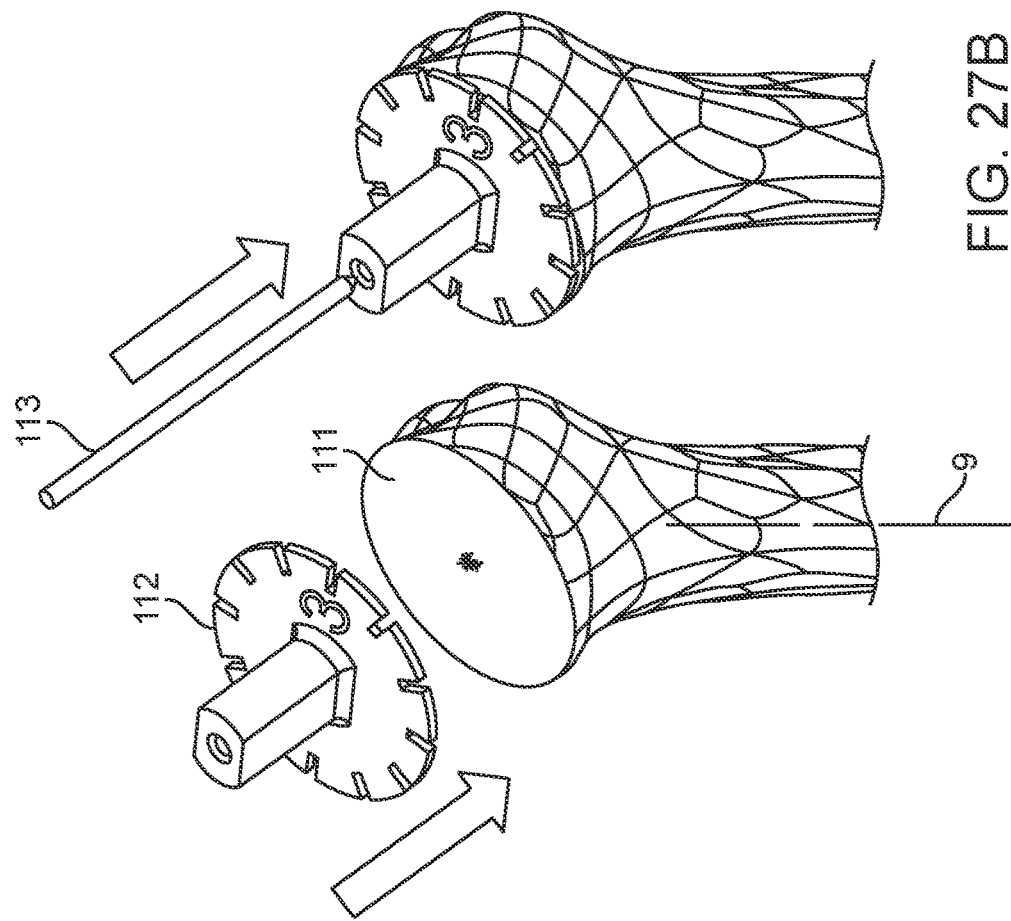
FIG. 27A  FIG. 27B  FIG. 27C  FIG. 27D

SHOULDER ARTHROPLASTY IMPLANT SYSTEM

CROSS-REFERENCE TO RELATED APPLICATIONS

The present application is a continuation of U.S. patent application Ser. No. 16/208,324, filed Dec. 3, 2018, which application is a continuation of U.S. patent application Ser. No. 15/445,658, filed Feb. 28, 2017, now U.S. Pat. No. 10,172,714, which claims the benefit of U.S. Provisional Patent Application No. 62/300,853, filed Feb. 28, 2016; the entire contents of which are incorporated herein by reference.

BACKGROUND OF THE INVENTION

Shoulder replacement surgeries were first performed in the 1950's in the United States to treat severe shoulder fractures. Over the years, the implants used in shoulder replacement surgeries have been improved to provide better outcomes and to expand the clinical indications for use to include shoulder arthroplasty for degenerative conditions. Modern shoulder replacement implants are generally of two designs; anatomic and reverse.

The anatomic shoulder implants are intended to restore the natural kinematics of the shoulder by replacing the humeral head and glenoid with similarly shaped prosthetic designs that recreate normal anatomy. The anatomic shoulder implant often has a spherical humeral head and a shallow concave glenoid that articulates with the spherical head. After the intact humeral head is resected, the anatomic shoulder implants have a stem configured to be securely placed down the shaft of the humerus and the spherical head is often fixed to the stem via a mechanical taper press fit. The glenoid prosthetic component, usually made from a polymer such as ultra-high molecular weight polyethylene (UHMWPE) is either cemented directly into the remaining intact glenoid or affixed to a metallic tray, which is secured to the native glenoid bone using bone screws, cement, or similar attachment methods.

The reverse shoulder is different from the anatomic shoulder implants in that the spherical surface is placed on the remaining intact glenoid and the concave articular surface is placed on the humerus. The reverse shoulder also has a stem configured to be securely placed down the shaft of the humerus. The polymer concave articular surface is fixed to the stem using a mechanical lock. The spherical head, in the reverse shoulder, is fixed to the remaining intact glenoid using a base plate.

Anatomic shoulder implants are used in patients to treat a variety of diseases that affect the shoulder joint and cause pain. A majority of these patients have osteoarthritis where the normal load bearing articular cartilage has eroded away. Reverse shoulders are generally used in patients with a weak, irreparably torn or insufficient rotator cuff. The rotator cuff is the anatomical term used to describe the group of muscles and their tendons around the shoulder joint that stabilizes the shoulder for proper motion of the joint. The reverse shoulder implants alter the kinematics of the joint and substitute for the function of the dysfunctional rotator cuff so that other muscles like the deltoid muscle can be used to lift the arm. Reverse shoulder implants may also be used in other severe cases, such as in cases of severe glenoid bone loss, where additional stability is required.

In cases where an anatomic arthroplasty has failed, it is sometimes appropriate to revise the anatomic arthroplasty to a reverse arthroplasty. To address this situation, a few shoulder arthroplasty systems have been introduced into the market that are "convertible" from an anatomic configuration to a reverse configuration. The main advantage of these convertible designs is that they obviate the removal of the existing anatomic humeral stem. Removal of the stem is technically difficult, associated with longer operative times, increased blood loss, and higher complication rates. Most designs are convertible by using an adaptor tray that allows the spherical head component of the failed anatomic arthroplasty to be exchanged with the adaptor tray which supports the concave humeral component of the reverse arthroplasty. These adaptor trays are also called "onlay" designs as the reverse poly cup is on top of the resection plane.

The adaptor trays used in these onlay designs are not always ideal because they add thickness in the joint that is potentially undesirable. This added thickness can create "over-tensioning" of the joint that over-tensions the soft tissue around the joint. Over-tensioning the joint can lead to decreased range of motion and also can cause acromial fractures, which are difficult to treat. Nonetheless, these are not the only complications that that can arise with current shoulder implants.

Another preventable complication that can occur in shoulder arthroplasty is bone loss due to stress shielding. Press-fit stem designs which achieve fixation in one region of the humerus may preferentially shield another area. The proximal metadiaphyseal and metaphyseal stress shielding are caused by stems which achieve secure fixation distally in the diaphysis. This may lead to a decrease in the physiologic loads in the proximal aspect of the humerus. Without this load, bone loss in this area can occur and potentially lead to eventual loosening of the implant. In addition, revising a failed arthroplasty that has resulted in significant proximal humeral bone loss is very difficult. There is increased fragility of the bone making fracture much more likely. Often, these fractures involve the bony attachments of the rotator cuff tendons which often compromises shoulder function. Stem designs that have a generally cylindrical shape are particularly problematic because they require a large number of sizes to address varying patient anatomy. Anatomically, the humeral head is not centered on the shaft (diaphysis) of the humerus. The stem designs that achieve fixation in the shaft must, by necessity, have multiple humeral head options with "offset" in order to recreate normal anatomy. As a result these stem designs also require a large inventory of different sizes and offsets to recreate the normal anatomy.

Current stems can also require more bone removal than is desired by the surgeon. Bone sparing designs may allow a greater amount of native bone to be preserved. For all of the above reasons, some new stem designs have the potential to be an improvement over existing stems.

Therefore, there is a need for improved shoulder arthroplasty devices and methods of use. At least some of the challenges described herein are addressed by the embodiments disclosed below.

SUMMARY OF INVENTION

The present application generally relates to medical devices, systems, and methods of use. More preferably, the present application relates to implants and systems used in surgical procedures, such as in a shoulder arthroplasty.

A shoulder arthroplasty implant system and method of use are disclosed but this is not intended to be limiting, and other uses are contemplated. The system is convertible between an anatomic configuration and a reverse shoulder configuration with an inlay design (i.e., no intermediate tray is required to switch between anatomic and reverse configurations, which may lead to less over-tensioning of the joint). The stem has been designed to primarily load the metaphysis in order to maximize bone compaction, reproduce a more physiologic load to the proximal humerus, thereby preventing stress shielding and loosening. An optimal shape and size of the system has been derived by a statistical model that reduces the number of sizes required to fit the patient population, and wherein each size may fit its portion of the population more closely. Additionally, the shape of the stem is designed to allow for the stems to be used in both left and right shoulders. Insertion of the stem into a prepared bone creates compaction of the bone adding to the stability of the implant.

In a first aspect, an implant for shoulder arthroplasty comprises a stem having a proximal portion, a distal portion, an anterior portion, a posterior portion, a medial portion, and a lateral portion. The stem has a size and shape for insertion into an intramedullary canal of a humerus bone. The humerus has a metaphysis and a diaphysis. The proximal portion of the stem comprises a concave taper decreasing in size in a direction extending from the proximal portion toward the distal portion, and the distal portion comprises a distal taper decreasing in size in a direction extending from the proximal portion toward the distal portion. The distal taper comprises a taper in a direction extending between the anterior portion and the posterior portion, and also the distal taper comprises a taper in a direction extending between the medial portion and the lateral portion. The shape of the stem is configured to load the metaphysis with a load greater than a load on the diaphysis.

The implant may further comprise a lateral fin, an anterior fin, and a posterior fin. The lateral fin may extend radially outward from the lateral portion of the stem. The anterior fin may extend radially outward from the anterior portion of the stem. The posterior fin may extend radially outward from the posterior portion of the stem. The lateral, anterior, and posterior fins may be configured to engage cancellous bone in the metaphysis or epiphysis to provide rotational stability to the stem. A lateral surface of the distal taper may comprise a convex curve extending in a direction from the proximal portion toward the distal portion, and a medial surface of the distal taper may comprise a concave curve extending in a direction from the proximal portion toward the distal portion. The taper in the direction extending between the anterior portion and the posterior portion may be symmetric about a medial plane of the implant so as to allow bilateral usage in the shoulder. The taper in the direction extending between the anterior portion and the posterior portion has a width which may be may be substantially equal to a diameter at a distal end of the concave taper on the proximal portion of the stem.

The implant may comprise a cylindrical extrusion disposed adjacent the proximal portion of the stem. A first point may be disposed on an anterior portion of cylindrical extrusion and a second point may be disposed on a posterior portion of the cylindrical extrusion. A third point may be disposed distally away from the first point and the third point may be disposed on an anterior portion of the distal taper. A fourth point may be disposed distally away from the second point and the fourth point may be disposed on a posterior portion of the distal taper. The first, second, third, and fourth points may define a first total included angle of a proximal portion of the distal taper. A fifth point may be disposed at a distal end of the stem and may be disposed on the anterior portion of the stem. A sixth point may be disposed at the distal end of the stem and may be disposed on the posterior portion of stem. The third, fourth, fifth, and sixth points may define a second total included angle of a distal portion of the distal taper. The second total included angle may be less than the first total included angle.

A distal portion of the stem may comprise an hourglass shaped cross-section with a width extending in a direction from the anterior portion toward the posterior portion that may be greater than a width at the medial portion or a width at the lateral portion. A distal portion of the stem may comprise a cutout section extending through the stem in a direction from the anterior portion toward the posterior portion, and the cutout may comprise medial and lateral edges which are offset from a medial surface and a lateral surface of the stem. The cutout may be configured to carry bone graft material.

The proximal portion of the stem may comprise a rim that comprises one or more protrusions extending outward therefrom, and the one or more protrusions may be configured to be received into a corresponding receptacle in an articular cup or a head component. The implant may further comprise a collar element disposed circumferentially around the proximal portion of the stem. The implant may also comprise one or more fenestrations disposed in the proximal portion of the stem. The one or more fenestrations may extend in a direction from the proximal portion toward the distal portion, and the one or more fenestrations may be sized to allow a surgical instrument to pass therethrough.

The implant may further comprise a tapered receptacle disposed in the proximal portion of the stem that is configured to receive a cooperating tapered protrusion disposed on an articular cup or disposed on a head component. The tapered protrusion may have a length that is sized to permit use in an anatomic or reverse arthroplasty, and the tapered protrusion may extend through the tapered receptacle thereby permitting an anatomic head component to be used with the stem. The implant may further comprise a coating that is disposed over at least a portion of the stem. The coating may be configured to promote bone ingrowth into the stem. The stem may be a single piece.

A system for shoulder arthroplasty may comprise any of the implants described herein and an articular cup coupled to the stem, or a head component coupled to the stem. The articular cup may be coupled directly to the stem without requiring an intermediate engaging element such as a tray. An apex of the cup may be disposed distally of a resection plane in the humerus.

In another aspect, a stemless implant for shoulder surgery comprises a body having a proximal portion, distal portion, and an outer surface. A cylindrical extrusion is substantially perpendicular to and adjacent the proximal portion of the body, and at least a portion of the outer surface is configured to contact bone. The outer bone contacting surface comprises a concave taper.

The concave taper may be defined by at least one radius revolved around a central axis of the cylindrical extrusion. The implant may further comprise a first fin extending radially outward from the bone contacting surface. The first fin may be configured to provide rotational stability and tapering from the proximal portion toward the distal portion. The first fin may have a width adjacent the proximal portion that is greater than a width adjacent the distal portion. The implant may further comprise a second, third, and fourth fin. The first fin may be disposed on a lateral portion of the implant, the second fin may be disposed on a medial portion of the implant, the third fin may be disposed on an anterior portion of the implant, and the fourth fin may be disposed on a posterior portion of the implant.

The cylindrical extrusion may comprise one or more protrusions extending outward therefrom, and the one or more protrusion may be configured to be received into a corresponding receptacle in an articular cup or a head component. The implant may further comprise a collar element disposed circumferentially around a proximal portion of the cylindrical extrusion. The implant may also comprise one or more fenestrations disposed in the proximal portion of the body. The one or more fenestrations may extend in a direction from the proximal portion toward the distal portion, and the one or more fenestrations may be sized to allow a surgical instrument to pass therethrough.

A system for shoulder arthroplasty may comprise any of the implants described herein and an articular cup coupled to the body or a head component coupled to the body. The articular cup may be coupled directly to the body without requiring any intermediate engagement element such as a tray. An apex of the cup may be disposed below a resection plane in a humerus bone.

In another aspect, a method for performing either anatomic or reverse shoulder arthroplasty on a shoulder having a humerus bone, comprises performing a proximal humeral osteotomy on the humerus, removing proximal bone from the humerus, and inserting an implant into the humerus and fixing the implant thereto. The implant loads metaphysis of the humerus, and the implant also loads the diaphysis of the humerus. The metaphysis load is greater than the diaphysis load.

The implant may comprise a stem having a proximal portion with a concave taper and a distal portion with distal taper.

Inserting the implant may comprise inserting the stem into the humerus without contact between the distal portion and cortical bone of the humerus. The implant may be stemless. The method may further comprise coupling an articular cup or a head component to the implant. The implant may comprise a stem and coupling the articular cup to the implant may comprise coupling the articular cup directly to the stem. An apex of the cup may be disposed below a resection plane in the humerus. Inserting the implant may comprise engaging one or more fins on the implant with the humerus. The implant may comprise a collar element that is disposed adjacent a proximal portion of the implant, and inserting the implant comprises advancing the collar element toward a proximal portion of the humerus. The stem may comprise one or more fenestrations disposed in the proximal portion of the stem, and the method may further comprise passing a surgical instrument through the one or more fenestrations.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The details of one or more variations of the subject matter described herein are set forth in the accompanying drawings and the description below. Other features and advantages of the subject matter described herein will be apparent from the description and drawings, and from the claims.

FIG. 27A, 27B, 27C, 27D shows the method of determining the center of the resection plane using a disk and pin.

DETAILED DESCRIPTION OF THE INVENTION

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

Disclosed is a shoulder arthroplasty system that is optionally convertible in use between an anatomic and a reverse shoulder implantation configuration. The system includes a short stem prosthesis that may provide several advantages. In the reverse shoulder configuration, the system includes an articular surface cup arranged in an inlay configuration on a receptacle of the stem. This may provide for a much more compactly sized system with respect to an onlay configuration. The system is configured to preferably achieve fixation in the metaphysis to preferably provide rotational and axial stability. The shoulder arthroplasty system may be implanted in both a press fit and a cemented configuration.

The system can be implanted using an installation technique that preferably removes as little bone as possible thereby conserving bone in the patient. It is designed on anatomy preferably based on a statistical shape model matching that of the humerus, as described in detail below. It should be appreciated that a statistical shape model is just an example, of a non-limiting means of analysis and that other means of analysis are within the scope of this disclosure.

Figure 1:
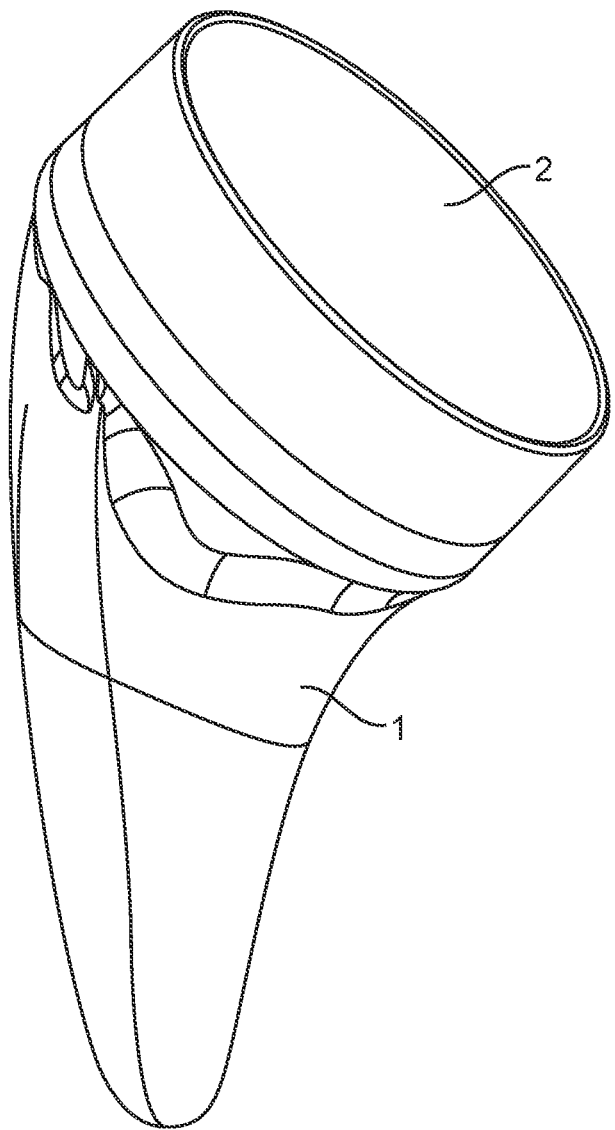
FIG. 1 shows a perspective view of the shoulder arthroplasty system in a reverse configuration.
Figure 2:
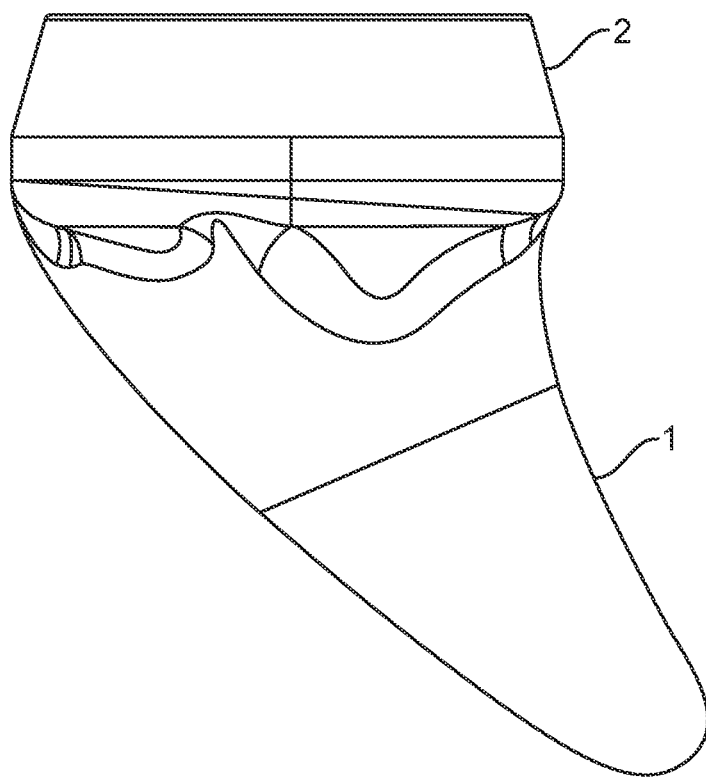
FIG. 2 shows a frontal view of the system with a cup in a reverse configuration.

FIG. 1 shows a perspective view of the shoulder arthroplasty system in a reverse configuration. The system includes a stem component 1 and a polymer cup 2 in a reverse configuration. FIG. 2 shows a frontal view of the system with the aforementioned stem component 1 that is sized and shaped to be inserted into the humerus. The stem has a monoblock or monolithic configuration that is a single piece structure. The single piece stem reduces manufacturing costs and hospital inventory requirements compared to a modular stem design. The cup 2 has an angled profile that provides a greater range of motion with less potential for notching which is loss of bone where the implant comes in contact with the glenoid, possibly during some movements. One of skill in the art will appreciate that the stem or stemless embodiments may be used with, or without, or in combination with, any of the other features described in this specification (e.g. fins, fenestrations, tapers, etc.).

The cup component 2 defines a curved articulating surface near to the resection plane. This provides minimal lateralization and inferiorization for a convertible prosthesis, which leads to a more anatomical reconstruction. The cup component 2 is interchangeable with the stem 1. A collection of multiple cup components 2 can be used for a single, corresponding stem component wherein each cup component of the collection has a particular articulating surface diameter and offset. This permits a user to select a cup component for use having a desired surface diameter.

Figure 3:
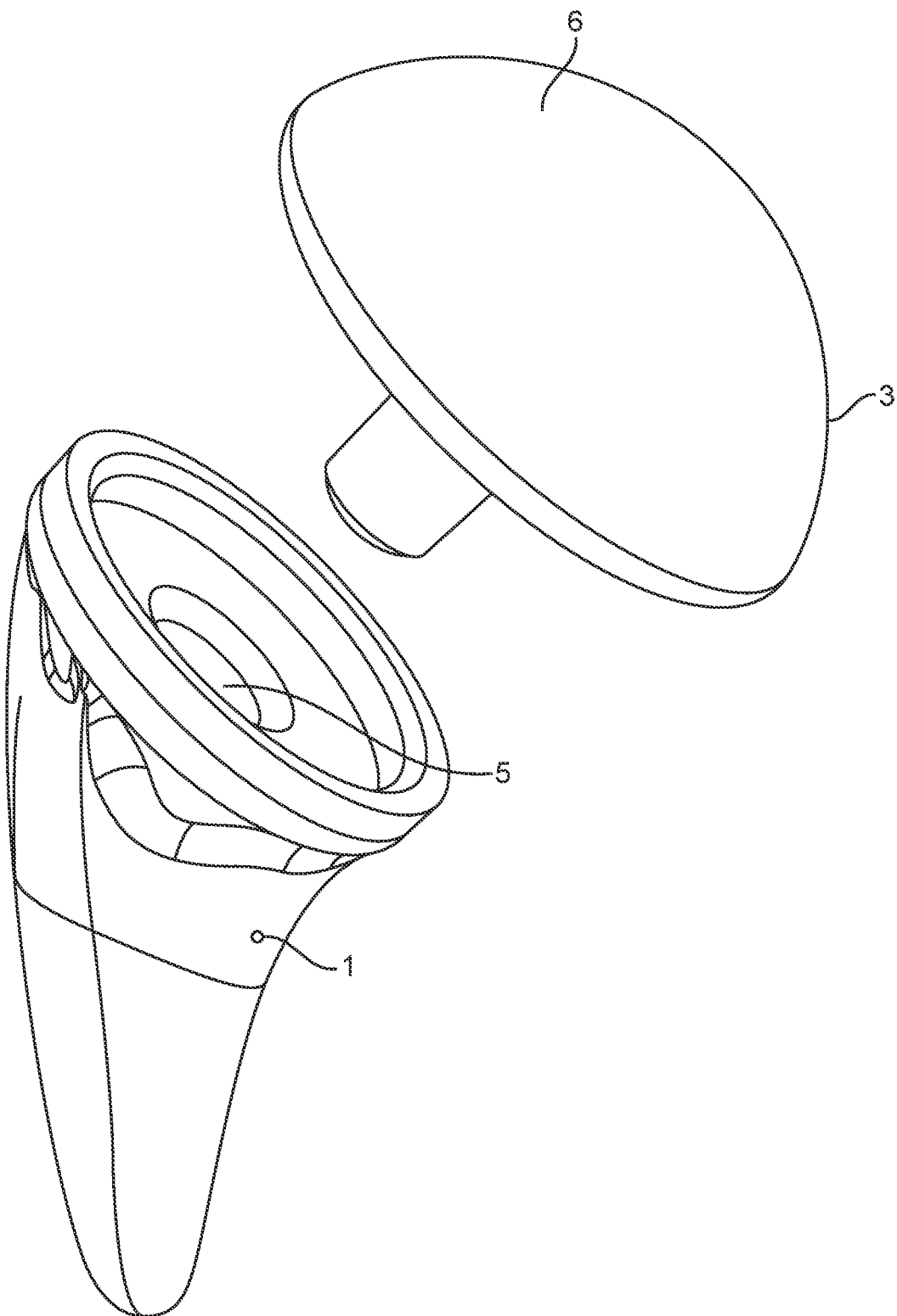
FIG. 3 shows a perspective view showing of the stem with head un-installed

FIG. 3 shows a perspective view of the shoulder arthroplasty system with a head component 3 uninstalled from the stem 1. The stem component 1 also includes a mechanical taper 5 that serves as a securing mechanism for the head component 3 and when secured to the stem 1. The anatomic head component 3 provides an articular surface 6 for anatomic shoulder reconstruction.

Figure 4:
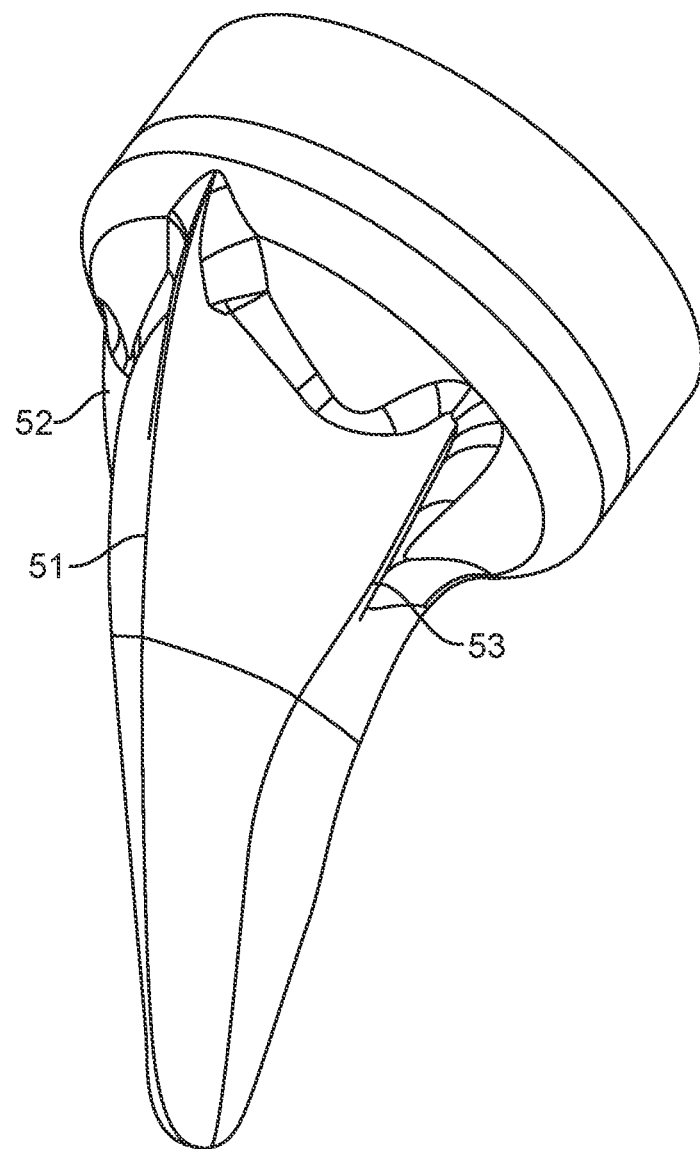
FIG. 4 shows a perspective view of the stem and cup.

FIG. 4 provides perspective views of the stem component 1. As described in detail below the stem has an anatomic shape that is configured pursuant to a statistical shape model. It should be appreciated that a statistical shape model is just an example, of a non-limiting means of analysis and that other means of analysis are within the scope of this disclosure. For example, other means of analysis including anatomic analysis, geometric analysis, anthropometric analysis, mechanical analysis, and kinematic analysis are within the scope of this disclosure. In this embodiment, the stem has three fin like protrusions, a lateral fin 51, anterior fin 52, and the posterior fin 53 configured to cut into cancellous bone in the metaphysis to provide rotational stability when the system is implanted in bone. The fins are configured to enhance rotational stability of the stem while avoiding cortical contact in the metaphysis. The anterior and posterior fins 52 and 53 may be used interchangeably when the stem is used in a left or right side of the patient.

Figure 5:
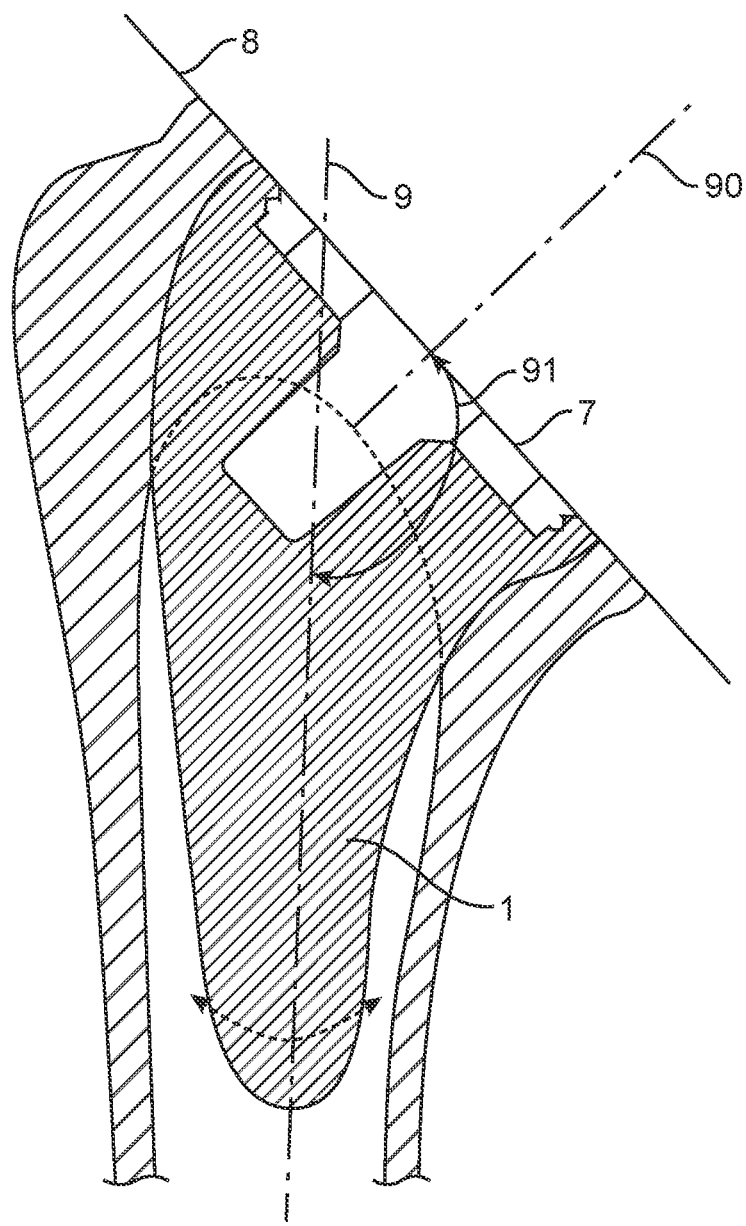
FIG. 5 shows an anterior cross-section of the stem installed in a humerus.

In FIG. 5, a cross section of the stem component inserted into the humerus is shown. The proximal end 7 of the stem 1 is positioned along a resection plane 8, which is the area exposed in surgery when the humeral head is surgically removed prior to preparation and implantation. An axis 90 normal to the resection plane 8 is at an obtuse angle 91 from the long axis of the bone 9.

Figure 6:
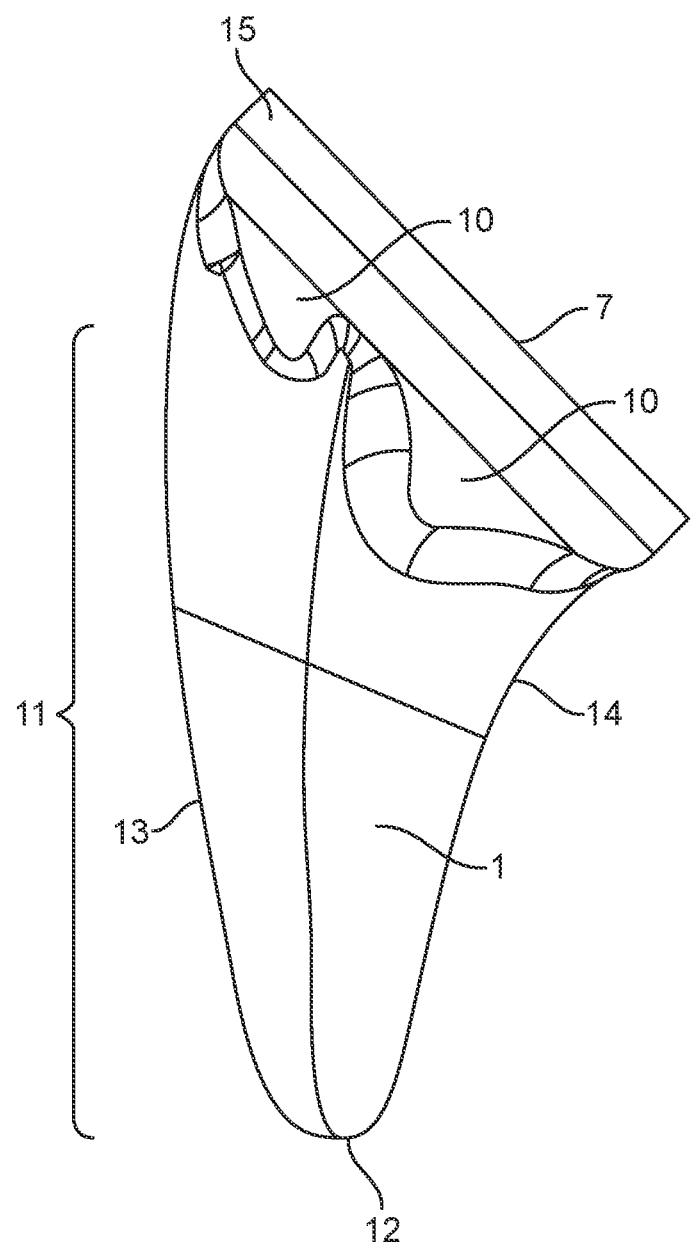
FIG. 6 shows a frontal view of the stem component.

FIG. 6 shows a frontal view of the stem component. The stem has an overall taper shape such that the implant generally increases in size proximally which improves wedged fixation. This configuration preserves bone by providing minimal removal of bone, especially in the greater tuberosity and humeral metaphysis. The design allows the stem to be centered proximally within the resection plane, which thereby allows the spherical head component of the anatomic configuration to be also centered on the resection plane, recreating normal anatomy. The outer bone contacting surfaces of the stem are configured to optimize the proximal bone loading in the proximal metaphysis of the humerus and reduce loading distally in the diaphysis. The taper shape has a proximal concave taper 10 that is generally conical and a distal taper 11 that is tapered in both the medial-lateral direction as well as the anterior-posterior direction. Additional details about the proximal and distal tapers are described elsewhere in this specification.

The stem has a proximal end 7, distal end 12, lateral side 13 and medial side 14. The proximal portion of the stem has a short cylindrical extrusion 15 perpendicular to the proximal end 7. In the preferred embodiment the cylindrical extrusion 15 is 2.7 mm and may range from 2.5 mm to 3 mm. While this is a preferred embodiment, the stem design may have other dimensions and would work without the cylindrical section where the proximal portion of the stem is conical right up to the proximal end 7. The design with the cylindrical extrusion 15 is preferred because this truncates the conical taper such that the diameter of the proximal end 7 is reduced for the same taper. In a preferred embodiment the diameter of the cylindrical extrusion ranges from 30 to 40 mm although other dimensions are possible. The diameter increases with increasing patient anatomy.

Figure 7:
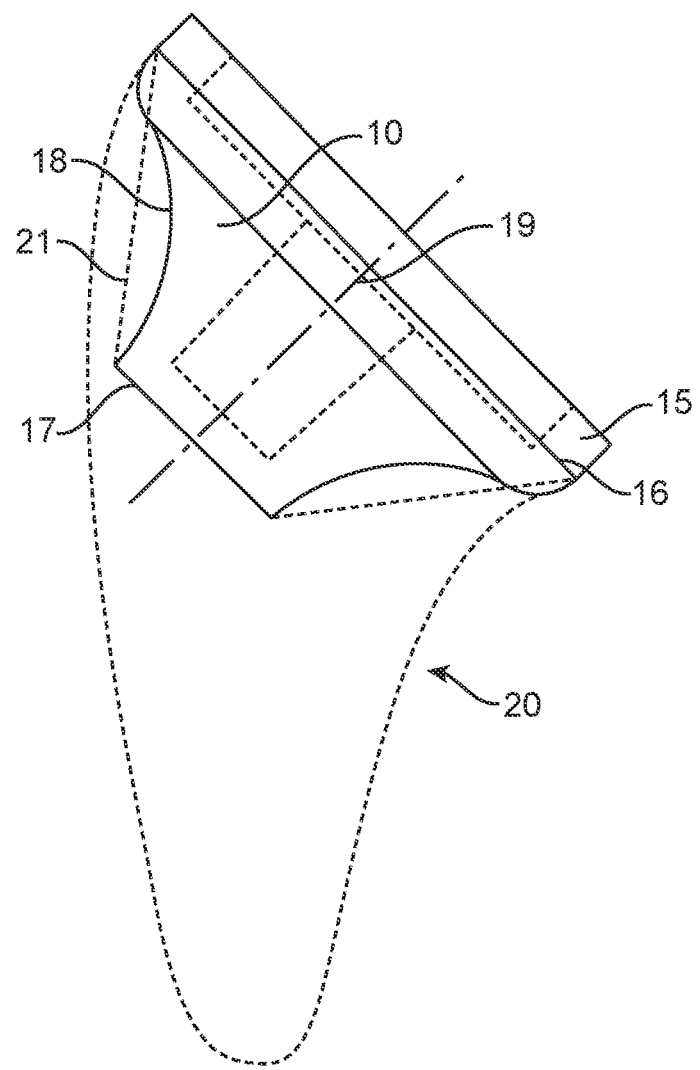
FIG. 7 shows a frontal view of the details of the proximal portion of the stem

FIG. 7 shows details of the concave taper 10 in the proximal portion of the stem. Distal to the cylindrical extrusion 15 the stem geometry transitions to a concave taper 10. The proximal end 16 of the concave taper 10 is congruent to the distal end of the cylindrical extrusion 15 and extends to a distal end of the taper 17. The concave taper 10 is defined by at least one radius 18 revolved around the axis 19 through the center of the cylindrical extrusion 15. The center of the radius 20 used to create the concavity is outside the cone created by the revolution of the straight line 21 created between proximal end 16 and the distal end 17 of the concave taper 10. In the preferred embodiment the length of the conical section from the proximal end 7 to the distal end 17 may be 18 mm but other lengths are possible. In alternate embodiments, the length of the conical section could range from 12-30 mm. The diameter of the proximal end of the concave taper 10 is preferably equal to the cylindrical extrusion 15 described above. The diameter of the distal end of the taper 17 in the preferred embodiment may be 9 mm and could range from 7 to 11 mm, although other sizes are also possible.

Figure 8:
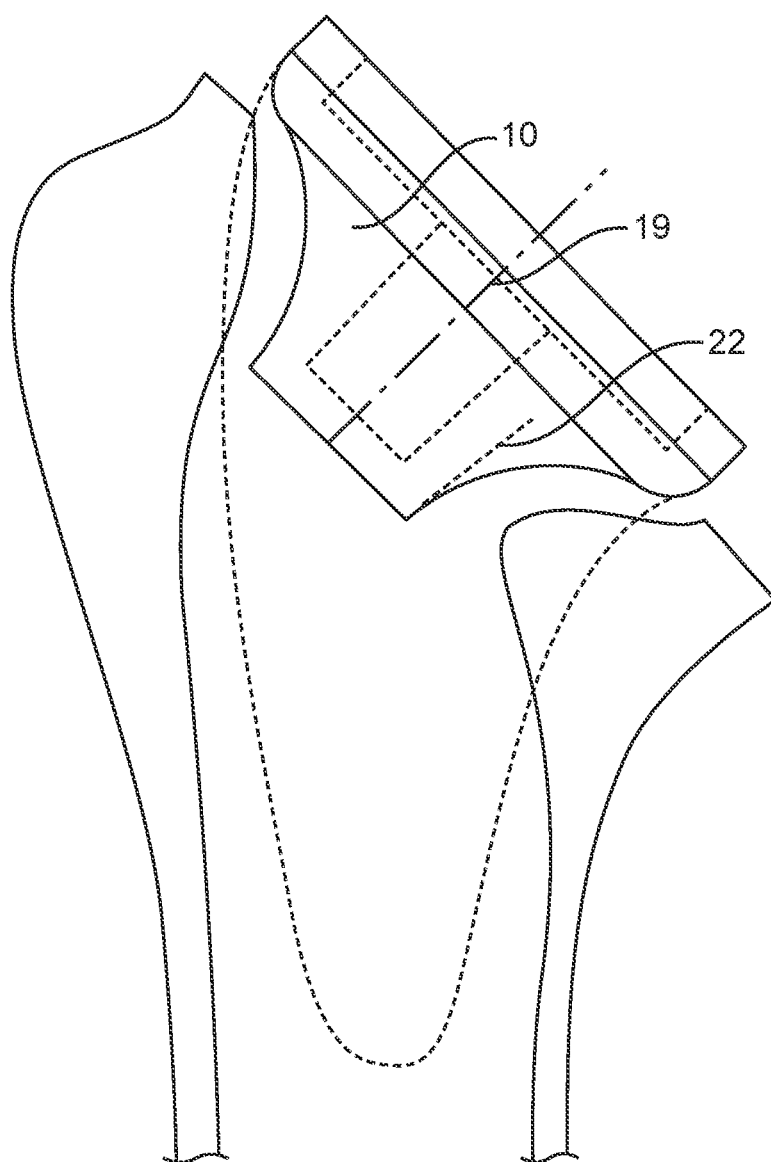
FIG. 8 shows details of the proximal portion of the stem in bone.

FIG. 8 shows the concave taper 10 and the interaction with the proximal bone during insertion of the stem 1. The concave taper 10 is designed to compact bone in the metaphysis during insertion. The compaction of bone is achieved when the stem is inserted into the bone. As the stem advances distally in the humerus, bone is displaced along the concave taper 10. The concave taper 10 is an advantageous shape because the angle formed between the axis 19 and a tangent line 22 to the concave surface increases as the stem is advanced in the bone. This provides ever-increasing compaction until final placement of the stem 1 is achieved.

Figure 9:
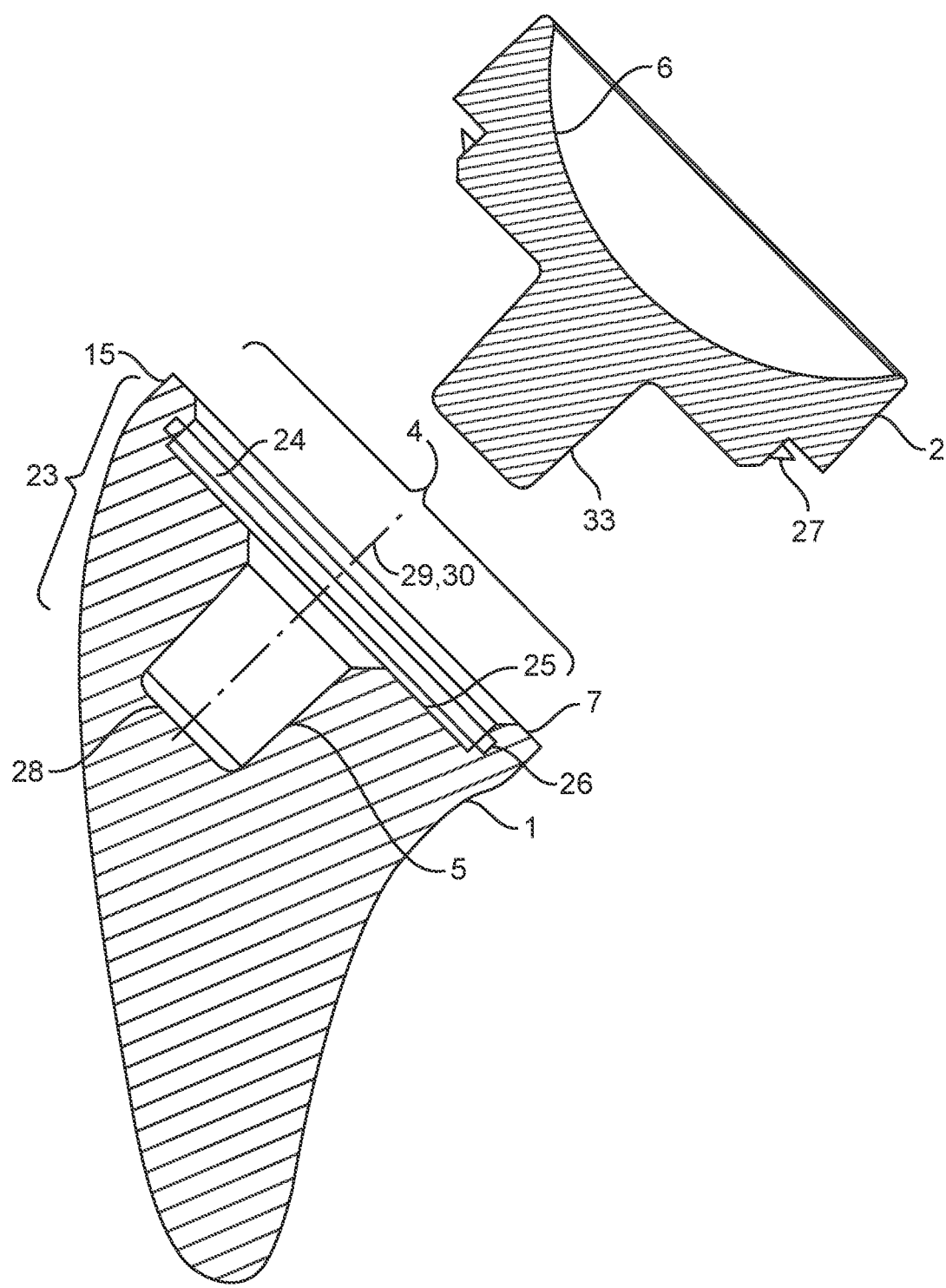
FIG. 9 shows a frontal cross-section of the stem and cup.

In the configuration shown in FIG. 9, the cup component 2 is uncoupled from the receptacle 4 of the stem 1. The cup component attaches primarily via a locking ring 27, but secondarily (and especially under load) with the taper 5. The proximal portion 23 of the stem houses the receptacle for the anatomic head for anatomic shoulder replacement and the articular cup 2 for reverse shoulder replacement. In the preferred embodiment, the stem has two receptacles; a female taper 5 and a cylindrical cavity 24. The cylindrical cavity 24 is concentric to the cylindrical extrusion 15. The cylindrical cavity 24 starts at the proximal end 7 of the stem and extends distally to flat surface 25 parallel to the proximal end 7. In the preferred embodiment, the cylindrical cavity 24 is 3.5 mm deep but it may be other depths. Between the proximal end 7 and the flat surface 25 an annular groove 26 is formed to receive the locking ring 27 of the articular cup 2. A male protrusion 33 has a taper that corresponds to the taper 5 in the female receptacle so that the two components engage one another.

FIG. 9 shows a cross section of the stem component 1 and articular cup 2. The female taper 5 is a conical tapered cavity that extends from the flat surface 25 of the cylindrical cavity 24 to a distal end 28. In the example shown, the axis of the female taper 29 is congruent with the axis of the cylindrical cavity 30. However, this embodiment is not limited to this and the axis may be offset from the cylindrical cavity 30 but preferably remains parallel to this axis. The female taper 5 is configured such that the diameter at the flat surface 25 is greater than the diameter at the distal end 28. The total included angle 31 of the female taper in a preferred embodiment is 4.6 degrees and the length is 12 mm, although other dimensions are possible. The female taper 5 in the stem receives a conical protrusion 32 in the anatomic head 3 and the conical protrusion 33 in the articular cup 2. When pressed together, the female taper 5 and the conical protrusion 33 become fixed to one another with an interference fit.

Figure 10:
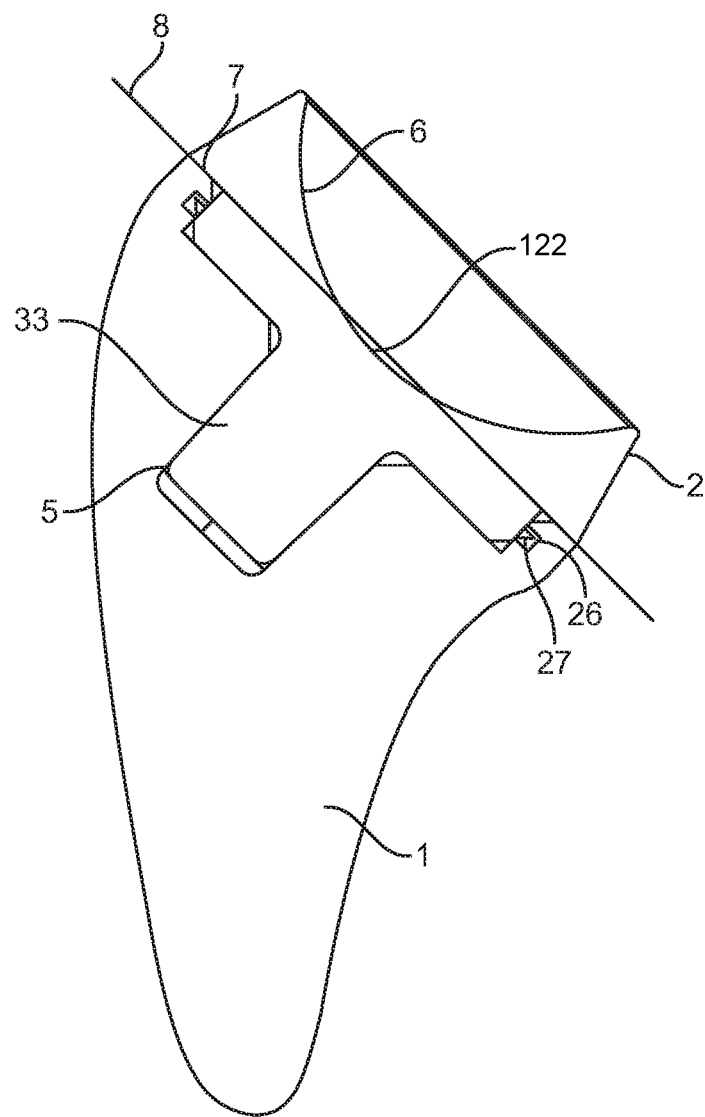
FIG. 10 shows a cross-section of the stem and cup assembled.

FIG. 10 shows a cross-section of the stem component 1 and articular cup 2 in an "inlay" configuration. The articular cup 2 is affixed to the stem by the locking ring 27 in the annular groove 26 and interference fit between the conical protrusion 33 and the female taper 5. In the preferred embodiment, the apex 122 of the concave articular surface 6 is distal to the proximal end 7 that sits flush to the resection plane 8. The inlay design greatly reduces the likelihood of over-tensioning the joint. Sufficient bearing thickness is maintained to support the loads and wear from patient activity.

Figure 11:
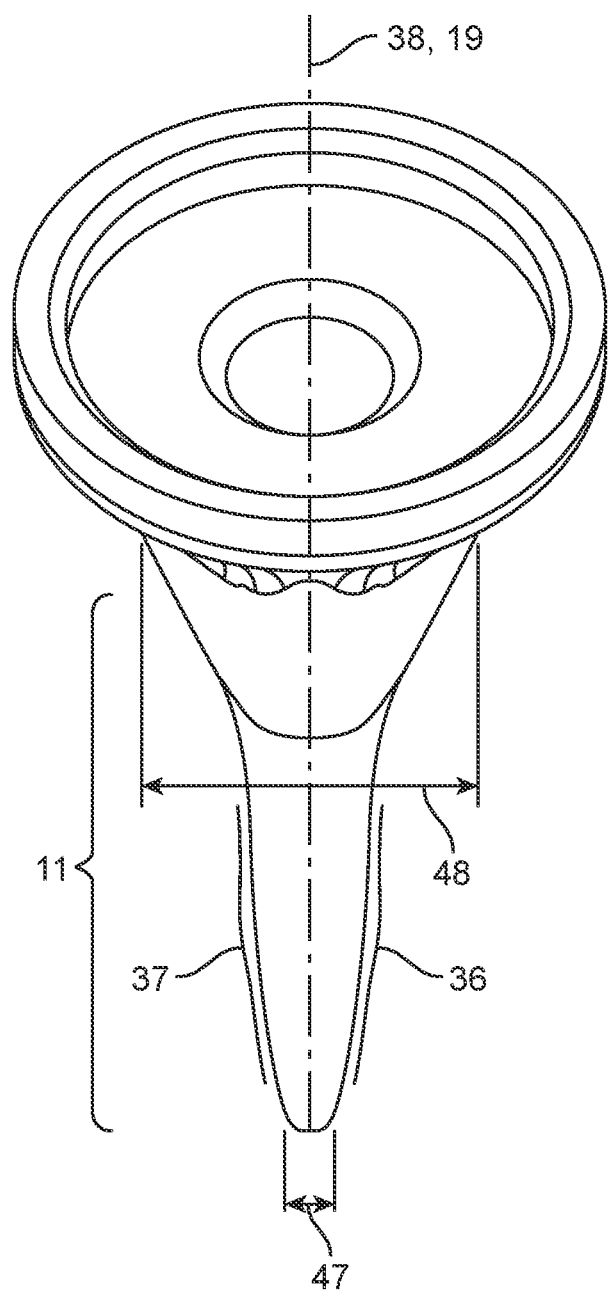
FIG. 11 shows a medial view of the stem component.

FIG. 11 shows a medial view of the stem without the articular cup 2 or anatomic head 3. The distal taper 11 has an anterior surface 36 and a posterior surface 37. In the preferred embodiment the distal taper 11 is symmetric about a plane 38 that is congruent with the axis 19 of the cylindrical extrusion. The distal taper 11 is generally tapered in both the medial-lateral direction and the anterior-posterior direction. The distal taper 11 has a medial-lateral width defined by the distance from the medial surface 34 to the lateral surface 35. The medial-lateral width decreases distally to create the medial-lateral taper. The distal taper 11 has an anterior-posterior width defined by the distance from the anterior surface 36 to the posterior surface 37. The anterior-posterior width decreases distally to create the anterior-posterior taper of the stem. The stem has a relatively thin cross-section. In the anterior to posterior direction, the thin cross-section is best described by the distal anterior-posterior width 47. The thin cross-section accommodates offset of the humeral head relative to intramedullary canal. This eliminates the need for left and right specific implants and further reduces inventory requirements. In the medial to lateral direction, the configuration is still thin enough to allow rotations to match resection cut without contacting cortical bone. In addition, the short length allows further flexibility in the location of the implant proximally (angular and position) as the distal stem is not constrained by cortical bone during implantation. It also preserves bone by eliminating the need to ream cortical bone.

Figure 12:
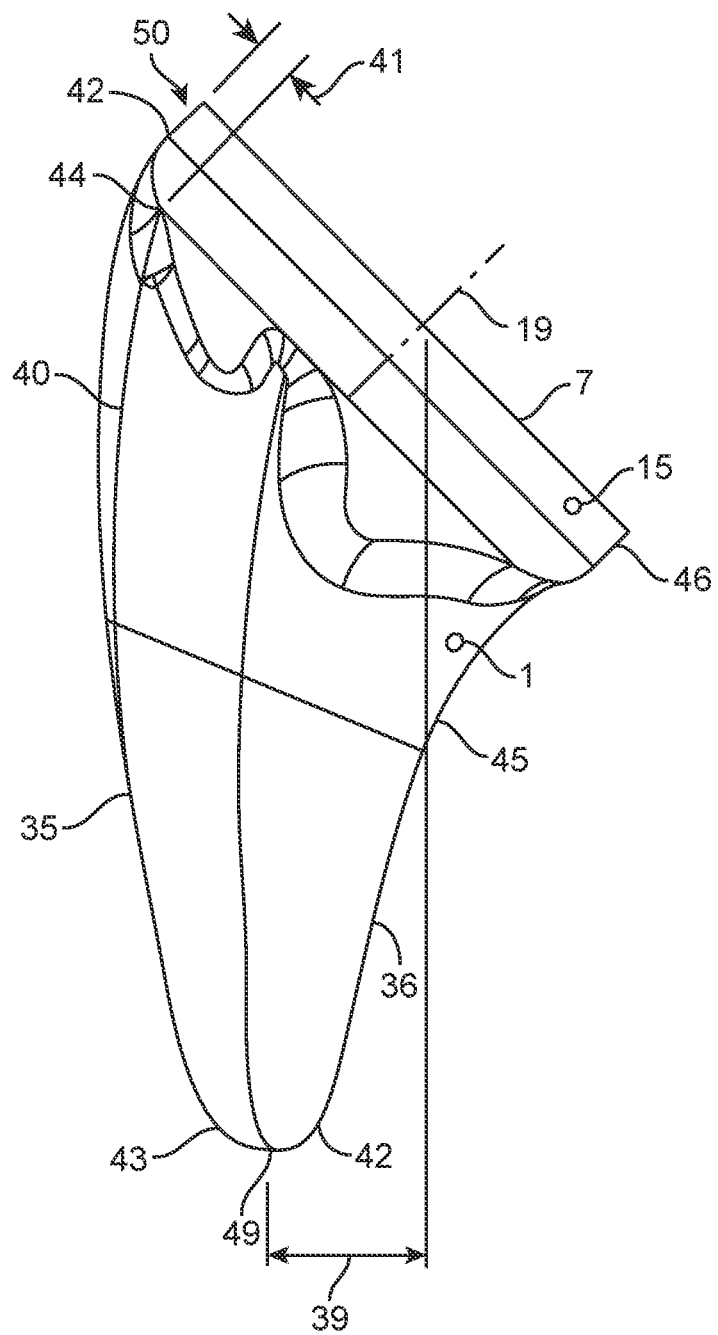
FIG. 12 shows a frontal view of the stem component

With reference to FIG. 11, the anterior-posterior taper of the distal taper 11 is configured to reduce loading of the cortical bone in the diaphysis and create wedge fixation. The anterior-posterior taper is symmetric about the medial plane 38 of the implant. The anterior-posterior width 47 at the distal end is less than the proximal width 48. In the preferred embodiment, the distal end of the distal taper is rounded in both the medial-lateral and anterior-posterior directions. In the preferred embodiment, the anterior-posterior width 47 at the distal end is 3.5 mm and the medial-lateral width at the distal end is 8, although other widths are possible FIG. 12 shows details of the medial-lateral taper geometry of the stem in a frontal view. The medial lateral taper geometry is configured to conform to but not contact the medial and lateral cortex of the humerus. The taper geometry may provide rotational stability of the implant. The medial-lateral taper is curved such that the distal end 49 of the stem 1 is offset laterally a distance 39 from a point intersecting the axis of the cylindrical extrusion and the proximal end 7. In the preferred embodiment, this lateral offset is 8.7 mm for the median size and ranges from 7-13 mm, although other distances are possible. The lateral surface 35 of the distal taper is defined by a convex curve 40 that extends from the proximal end to the distal end 49. The curve starts at a medial offset 41 from the most lateral edge 42 of the proximal end 7 and extends to farthest lateral edge of the distal portion 43. The medial offset 41 of the lateral surface 35 is the distance from the lateral edge of the cylindrical extrusion 42 to the proximal end of the lateral surface 44. The offset 41 provides space for a lateral fin like protrusion that is described in detail below. The curve of the lateral surface 35 is comprised of at least one radius. The medial surface 36 of the distal taper 11 is defined by a concave curve 45 that extends from the proximal end 7 to the distal end 49. The curve 45 starts at the medial most edge 46 of the proximal end 7 and extends to the farthest medial edge 92 of the distal end. It should be noted that the tapered section along the medial edge may also be interpreted as a fin-like protrusion and is described in further detail below. The medial curve 45 is comprised of at least one radius. The medial-lateral taper increases in width to the distal end of the cylindrical extrusion 15. The curved medial surface is sized and shaped to reduce fracture risk by spreading implantation forces over a larger area during implantation. The total length of the implant from the center of the proximal end 7 to the distal tip ranges from 44 mm to 48 mm although other lengths are possible. The overall length of the implant from the most distal point 49 to the farthest point superior point 50 ranges from 55 mm to 61 mm although other lengths are possible.

Figure 13:
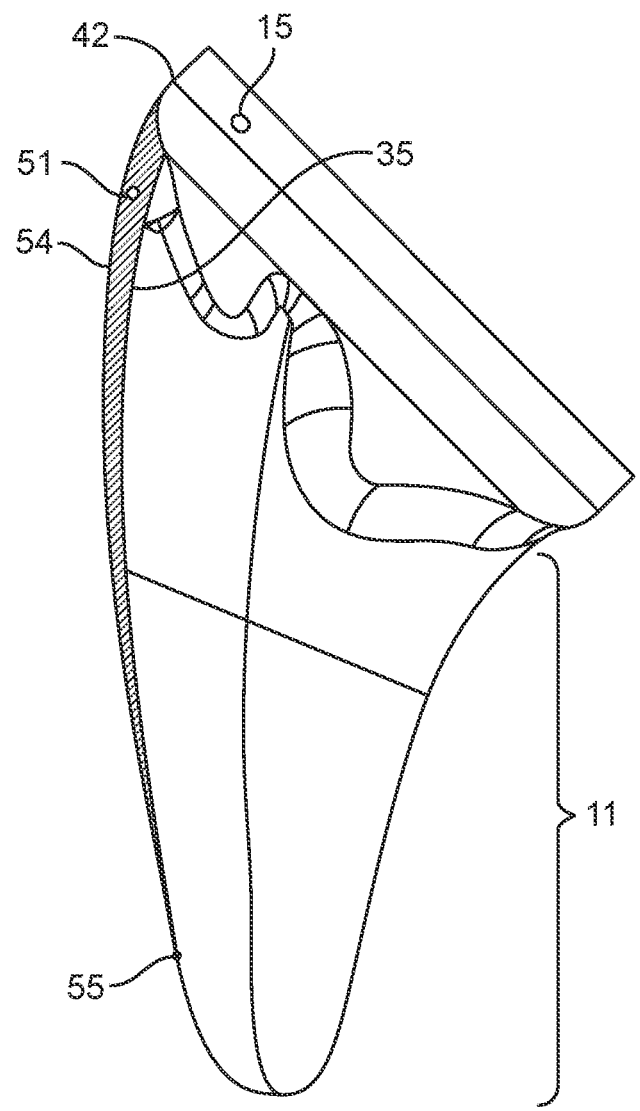
FIG. 13 shows a frontal view of the stem component and lateral fin details.

FIG. 13 shows details of the lateral fin 51. The lateral fin is defined by a lateral edge 54 that follows a convex curve from the lateral most edge 42 of the cylindrical extrusion 15 to a point 55 that is tangent to the lateral surface 35 of the distal taper 11. The convex curve can be defined by at least one radius.

Figures 14A, 14B:
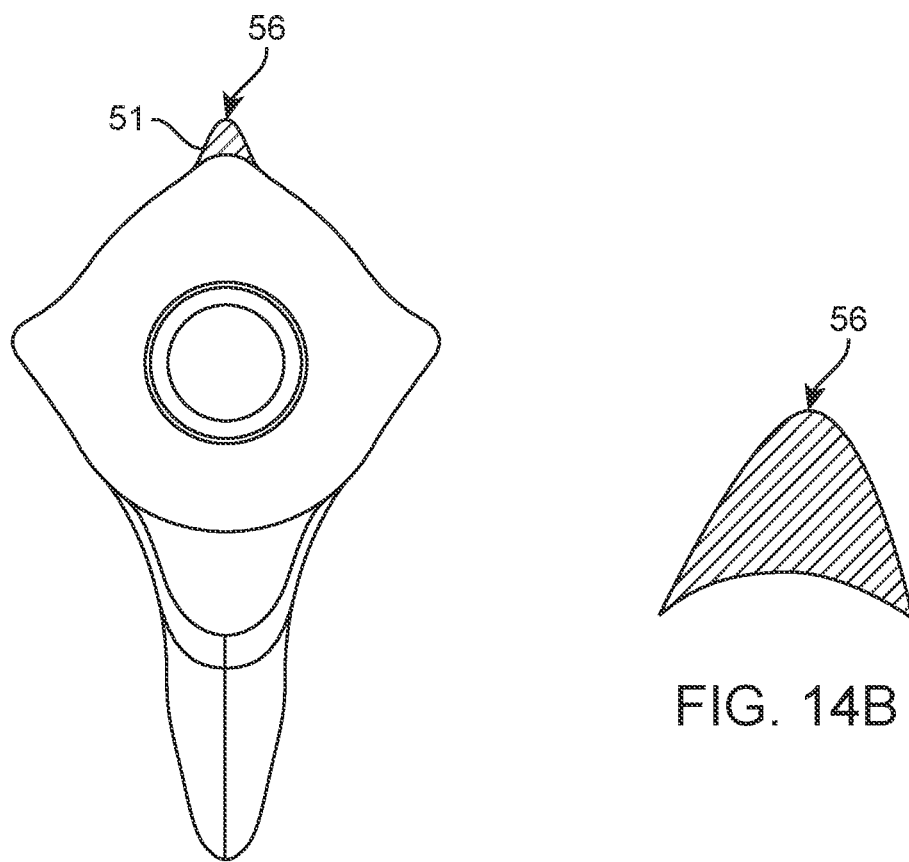
FIG. 14A shows a cross-section of the stem component.
FIG. 14B shows a detailed cross-section of the lateral fin.

The cross-section of the lateral fin protrusion 51, shown in FIGS. 14A-14B, is substantially triangular in the preferred embodiment. The apex 56 of the triangular cross-section is congruent with the lateral edge 54 previously defined. Alternate embodiments, may include rectangular or hemispherical like cross-sections.

Figure 15A:
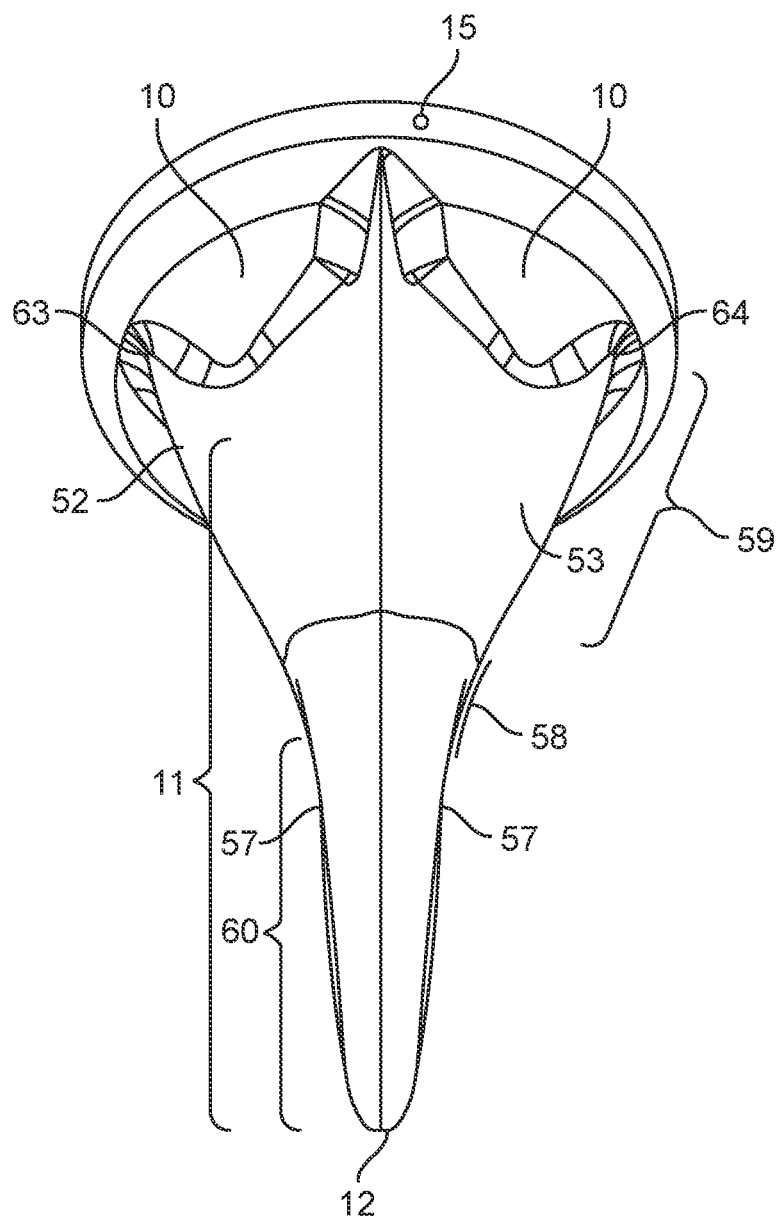
FIG. 15A shows a lateral view of the stem component.
Figure 15B:
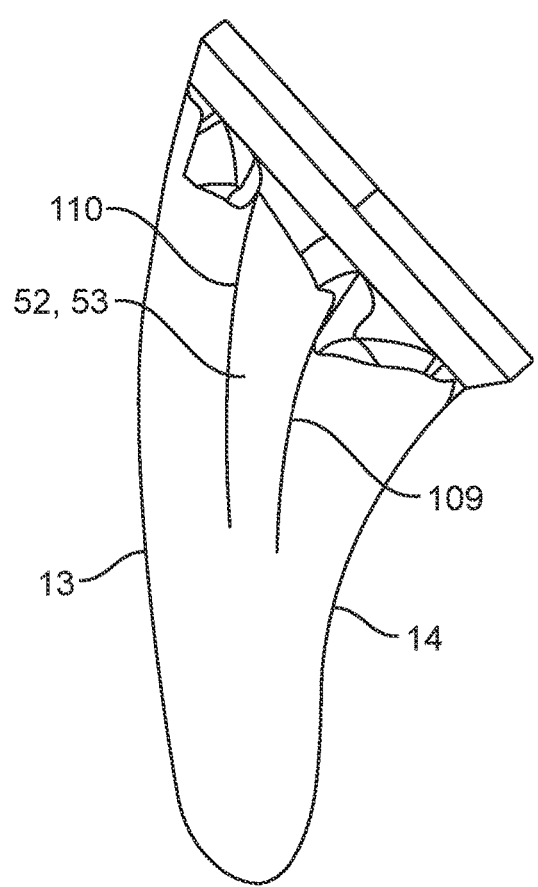
FIG. 15B shows a frontal view of an alternate anterior/posterior fin geometry.
Figure 15C:
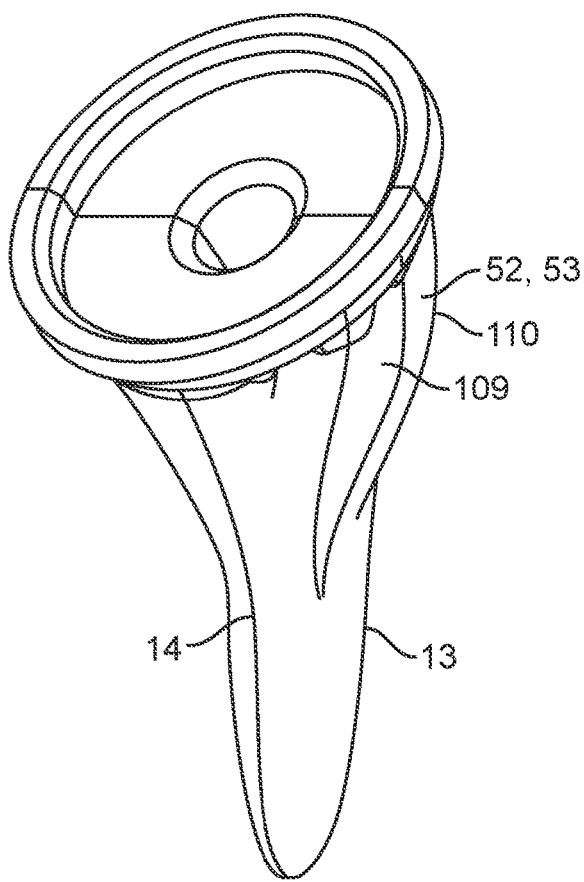
FIG. 15C shows a perspective view of the same embodiment.

FIG. 15 shows a lateral view of the stem component. The anterior and posterior fins 52, 53 extend from a point 57 on the distal taper 11 that is distal to the concave taper 10 and proximal to the distal end 12 of the stem. The anterior and posterior fins 52, 53 extend from the point 57 to meet the cylindrical extrusion 15. In the preferred embodiment, the anterior and posterior fins 52, 53 are concave at the distal end of the fin 58 and convex at proximal end of the fin 59. The concave portion of the fin is tangent to the anterior/posterior surface 60 of the distal taper 11 at the distal end of the fin 58. The convex portion of the fin is tangent to the cylindrical extrusion 15 at the proximal end of the fin 59. FIG. 15B and FIG. 15C show an alternate embodiment of the anterior and posterior fins 52,53. In the alternate embodiment the anterior and posterior fins have a medial surface 109 and a lateral surface 110. The medial surface 109 and lateral surface 110 are substantially parallel to each other. In additional fin geometries the anterior and posterior fins may be located closer to the lateral side 13 than the medial side 14.

Figure 16A:
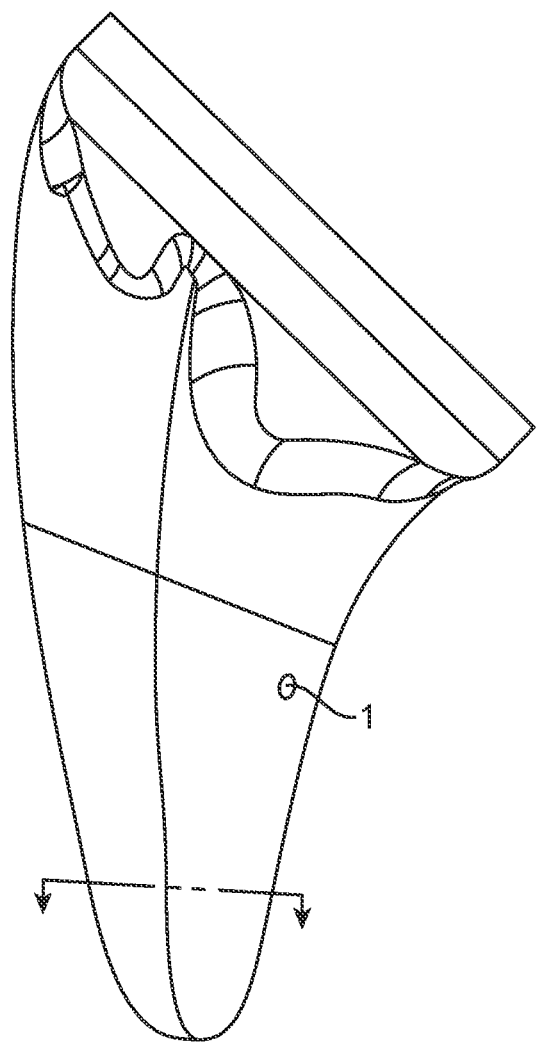
FIG. 16A shows a frontal view of the stem.
Figure 16B:
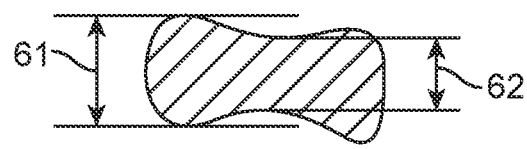
FIG. 16B shows the distal cross-section of the stem.

FIG. 16B, shows in the preferred embodiment, the part of the stem 1 distal to the anterior and posterior fins of the stem has an hourglass like cross-section. The cross-section is shaped such that anterior-posterior width 61 at the medial and lateral sides is greater than the center 62 of the cross-section. This preserves bone while keeping any bone contacting surfaces at the medial and lateral edges with sufficient contact area to support implant loads and avoid compromising the internal cortex.

Figure 17A:
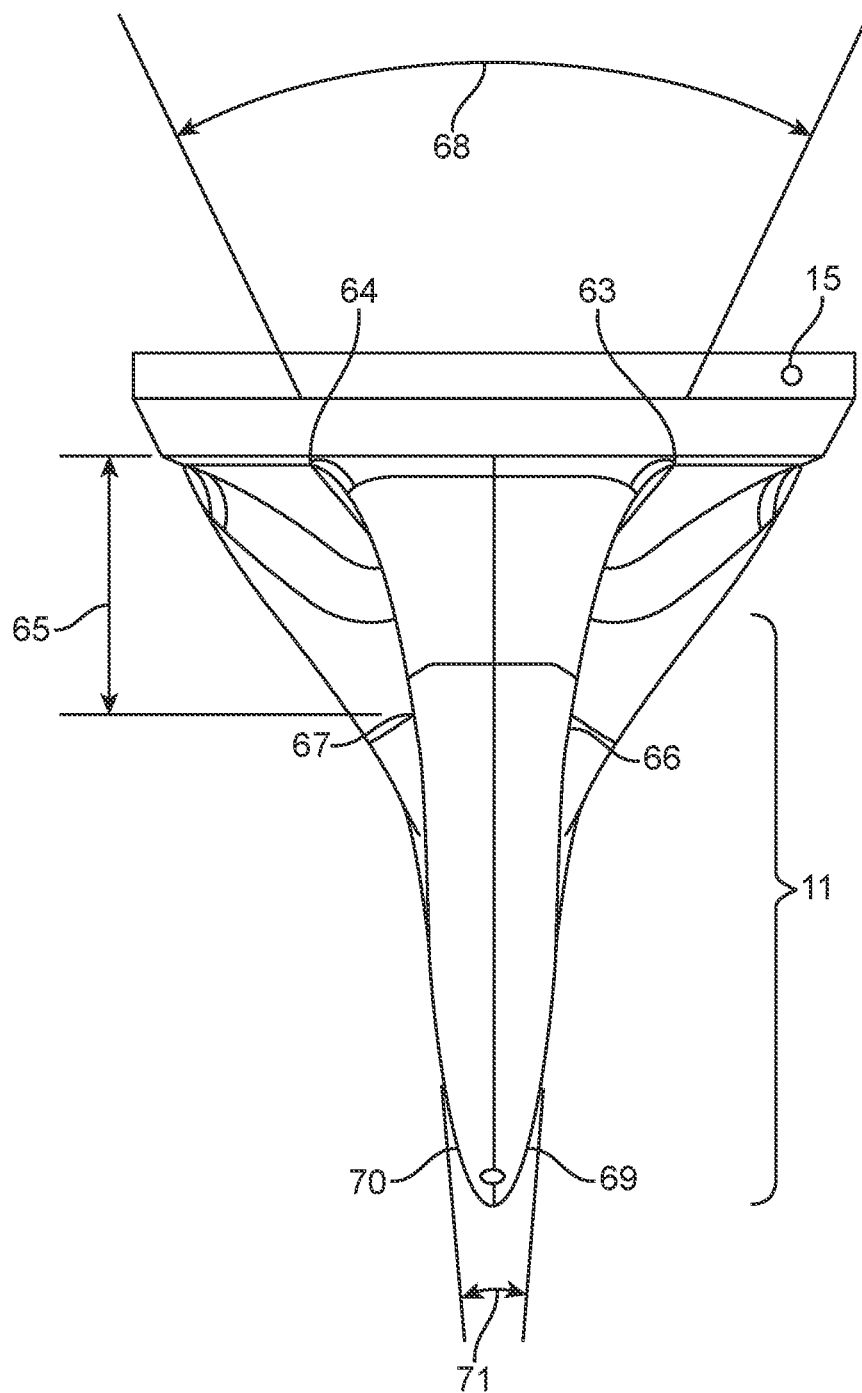
FIG. 17A shows a medial view of an alternate embodiment of the medial surface geometry.
Figure 18:
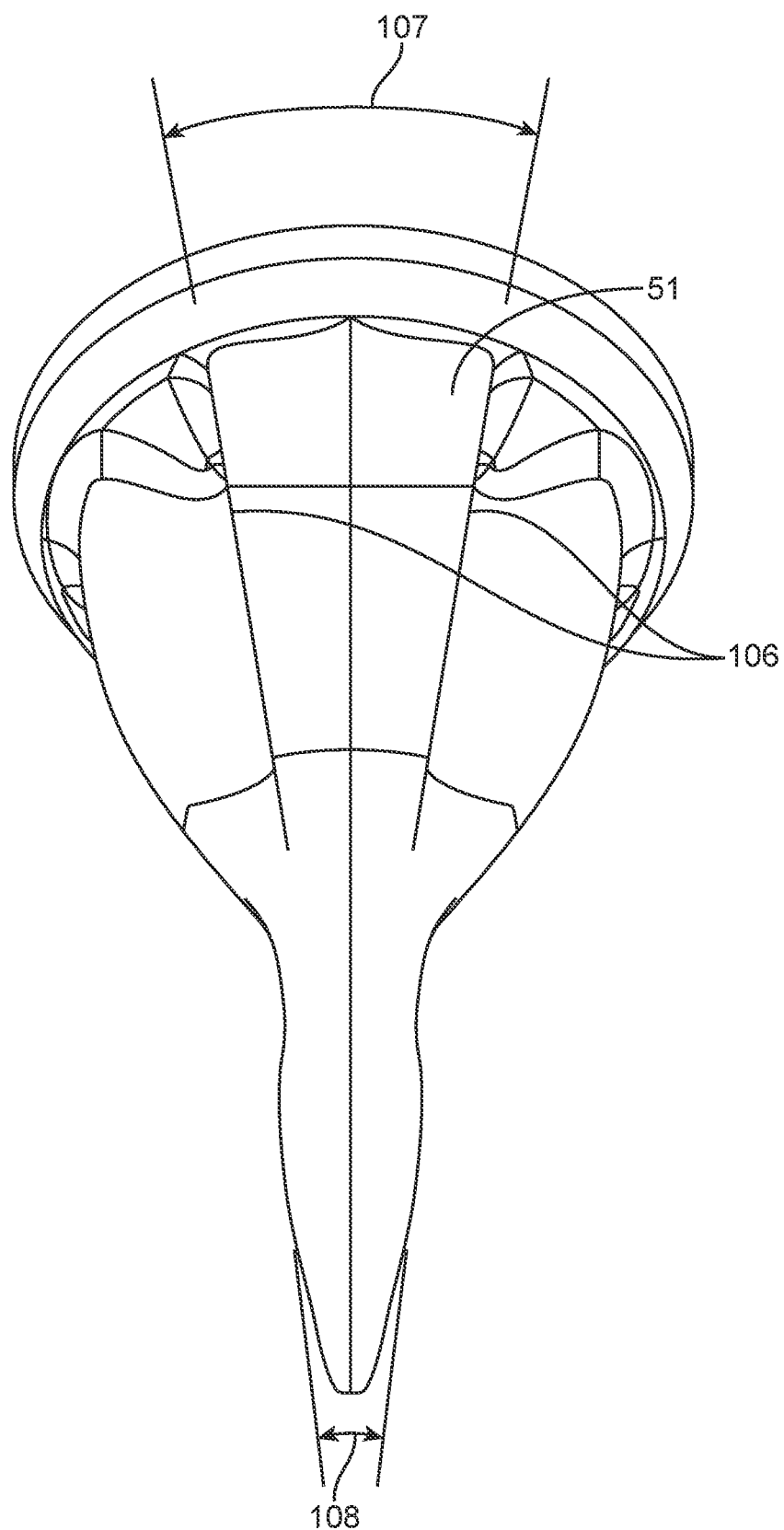
FIG. 18 shows a lateral view of an alternate embodiment of the lateral fin.

FIG. 17A shows an alternate embodiment of the anterior-posterior taper geometry of the taper. This embodiment provides a larger bone-contacting surface on the medial and lateral surfaces and increases the wedge fixation in the metaphysis of the bone. The distal taper, in the alternate embodiment, has an anterior posterior width at the proximal end defined by the distance between an anterior point 63 on the cylindrical extrusion 15 and a posterior point 64 on the cylindrical extrusion 15. At a distance 65 distally along the distal taper 11, the anterior-posterior taper is further defined by a second width defined by the distance between an anterior point 66 and a posterior point 67. These 4 points define a total included angle 68 of the proximal portion of the distal taper 11. A distal total included angle can be defined by the second width, the distance between points 66 and 67 and the anterior 69 and posterior 70 points at the distal end 12 of the stem 1. The total included angle 71 of the distal portion of the distal taper is less than the proximal total included angle 68. FIG. 17B shows a similar geometry but on the lateral fin 51. The lateral fin 51 has anterior and posterior surfaces 106 that form an angle 107. The angle 107 is greater than the angle formed by the distal taper angle 108.

Figure 19:
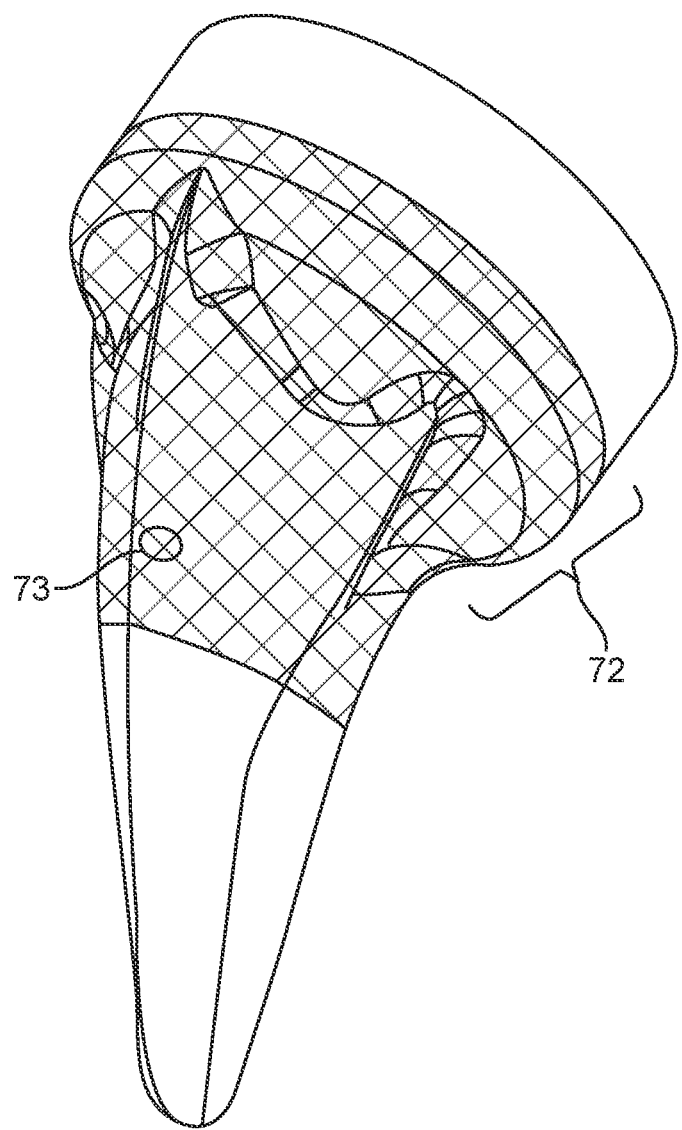
FIG. 19 shows a perspective view of the preferred bone growth coating placement.
Figure 26:
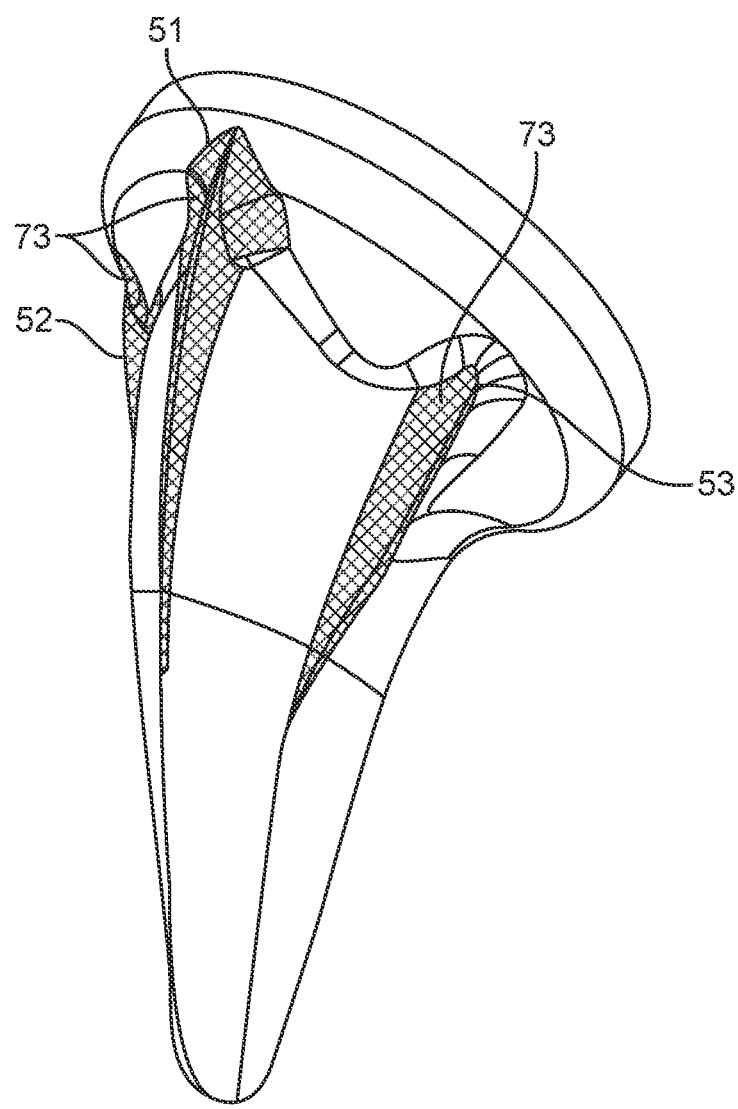
FIG. 26 shows an alternate bone growth coating placement.

In a preferred embodiment, FIG. 19, the proximal bone contacting surfaces 72 have a coating 73 for additional boney in-growth Coatings may include plasma spray titanium, hydroxyapatite or similar coatings known in the art to enhance bone growth. In the preferred embodiment, the proximal 19-21 mm of the stem is coated. However, additional embodiments could include coating the entire stem or any sections. FIG. 26 shows one such embodiment of the placement of the bone growth surface where only the fins 51, 52, 53 of the stem are coated with a bone growth coating 73. The proximal section of the stem is grit blasted and the distal portion is polished smooth.

Figure 20A:
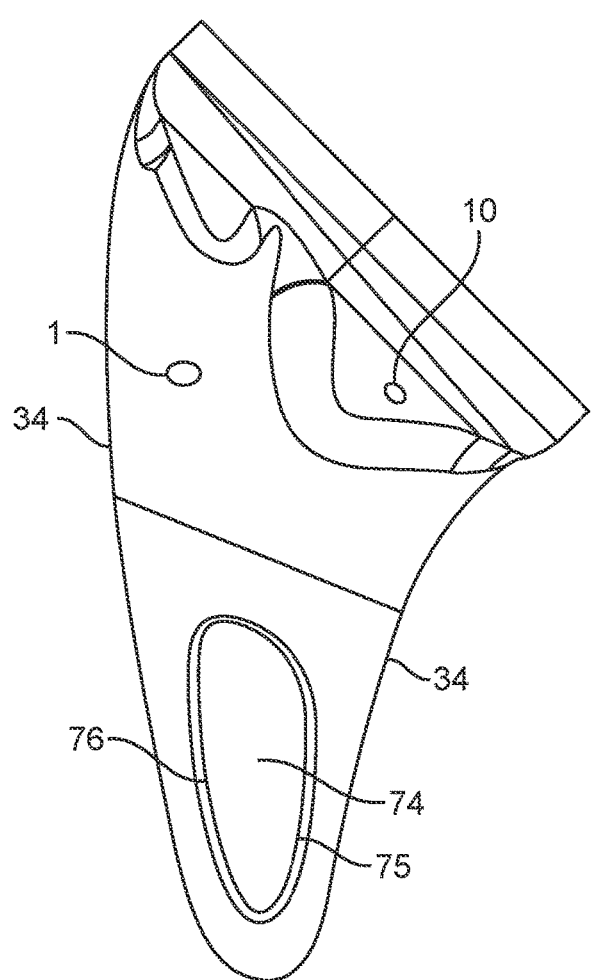
FIG. 20A shows a frontal view of alternate stem geometry with a cutout for additional bone graft placement.
Figure 20B:
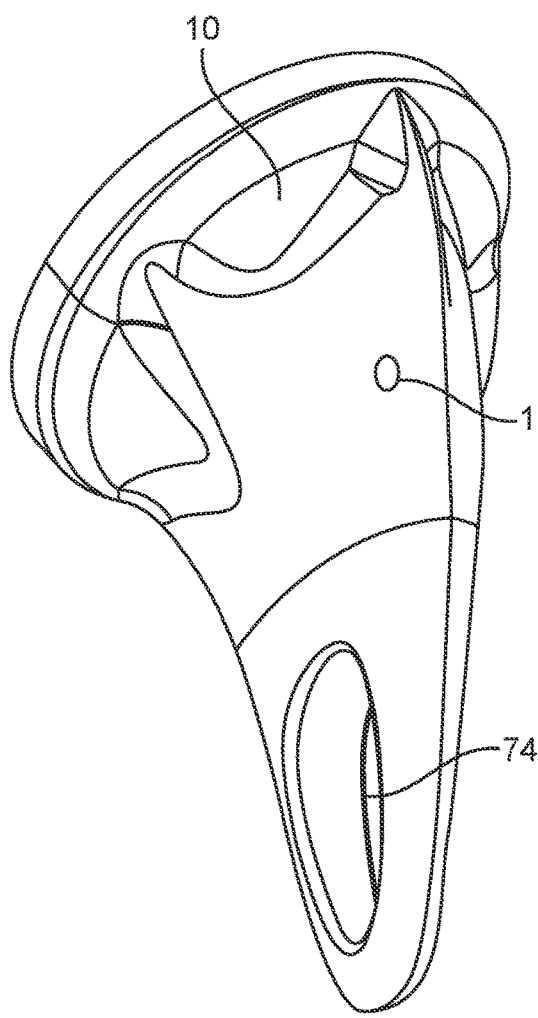
FIG. 20B shows the same embodiment in a perspective view.

FIGS. 20A and 20B shows an alternative embodiment of the distal portion of the stem that has a cutout 74 to contain additional bone graft. The medial 75 and lateral 76 edges of the cutout 74 is offset from the medial 34 and lateral surfaces 35 of the stem and extends through the stem 1 in the anterior-posterior direction. In this embodiment, the proximal extent of the cutout 74 is distal to the concave taper 10. The cutout may be used in any stem embodiment described herein.

Figure 21:
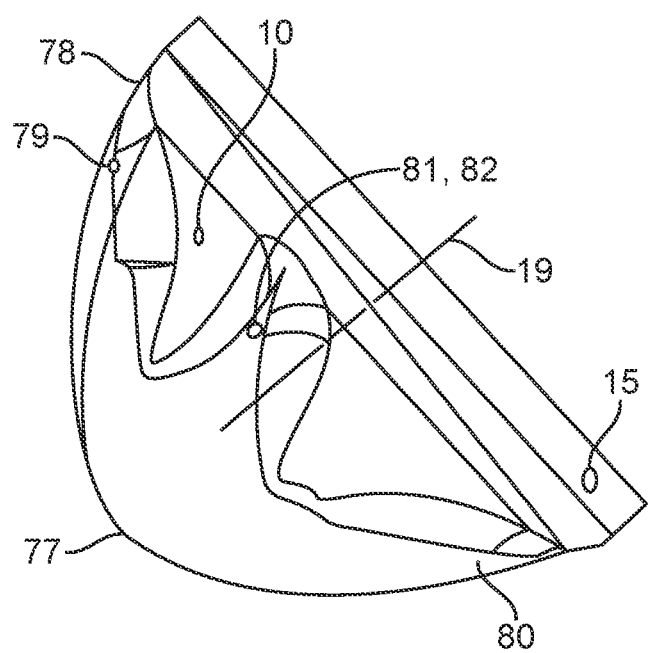
FIG. 21 shows a frontal view of a stemless configuration.

FIG. 21 shows an alternate embodiment of the stem, which does not have a distal taper as described in previous embodiments. This configuration is commonly called a "stemless" or "canal sparing" implant. The device is surgically implanted in the same manner as the longer, "stemmed", design, and therefore provides the surgeon with an additional option without adding complexity. Stemless designs can be used to further enhance positional flexibility proximally when metaphyseal fixation is adequate and cementation is not required. In the stemless design, like the "stemmed" design, the outer bone-contacting surface of the stem has a concave taper 10. The stemless design, like the stemmed design, has a cylindrical extrusion 15 perpendicular to the proximal end 7. The concave surface is defined by at least one radius that revolves around the axis 19 created by the cylindrical extrusion 15. The stemless design also includes at least one fin-like protrusion for rotational stability. As previously described, the fin-like protrusions extend from the distal portion of the stem to meet the proximal cylindrical section. The fins taper from the distal end 77 to a greater width at the proximal end of the fin 78. In a preferred embodiment, fins are located at the lateral 79, medial 80, anterior 81 and posterior 82 aspects of the implant.

Figure 22A:
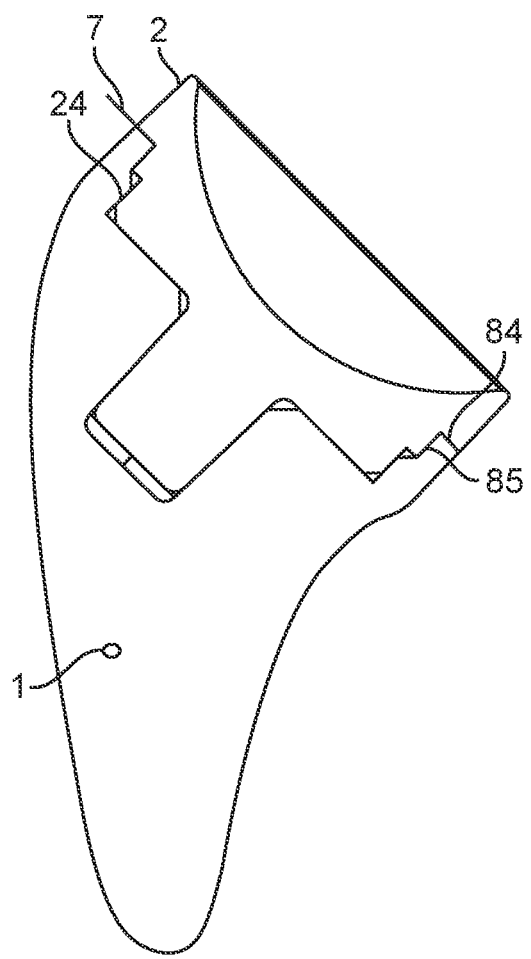
FIG. 22A shows a cross section of an alternate embodiment of the stem component with protrusions.
Figure 22B:
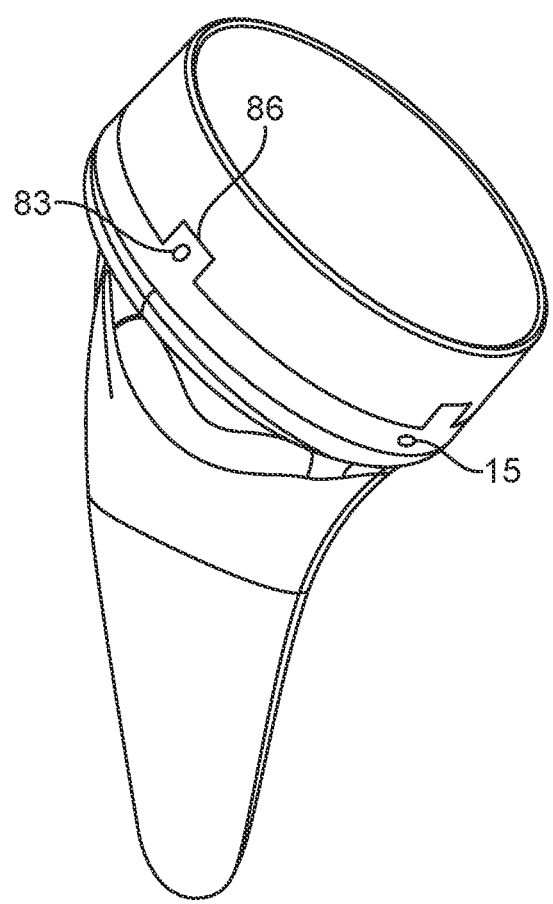
FIG. 22B shows a perspective view of the same embodiment.

FIG. 22A shows a cross-sectional view of an alternate embodiment of the proximal end where the stem 1 has at least one protrusion 83 on the rim 84 of the proximal end 7 to prevent rotation of the articular cup 2. A preferred arrangement is four protrusions distributed evenly along the rim 84 of the proximal end 7. The protrusion 83 extends from proximal end 7 of the stem. A rim 84 is created by the outer diameter of the cylindrical extrusion 15 and the cylindrical cavity 24. FIG. 23A shows the protrusion extends radially from the inner surface 85 created by the cylindrical cavity 24 to the outer surface of the cylindrical extrusion 15. However, alternative embodiments could include the protrusion only extending part of the way from the cylindrical cavity 24 to the cylindrical extrusion 15. The articular cup 2 for a reverse shoulder would have mating indents 86, shown in FIG. 22B to receive the protrusions 83. Any embodiment disclosed herein may include some or all of these features.

Figure 23:
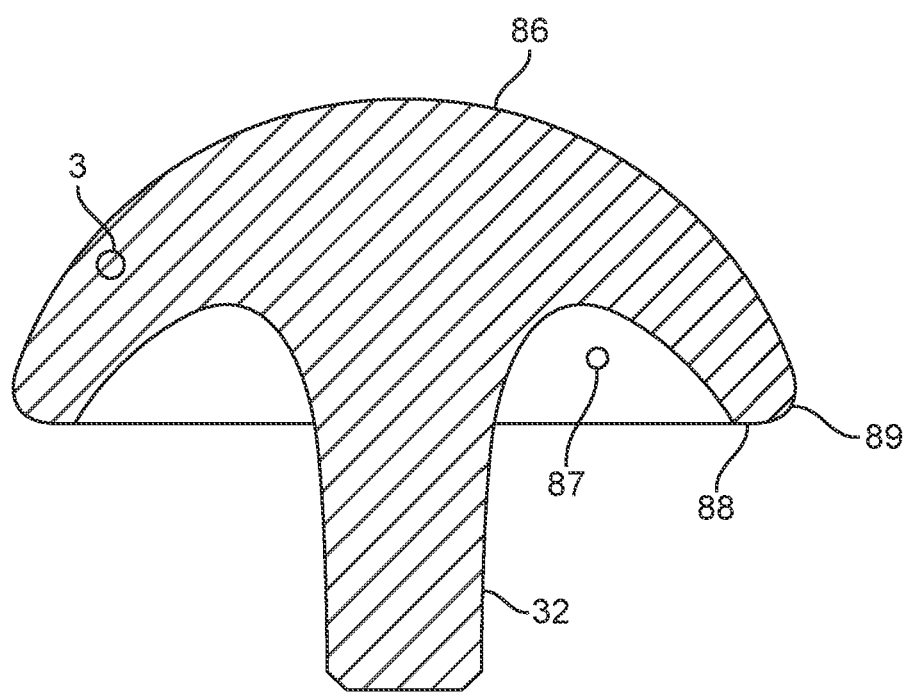
FIG. 23 shows a cross-section of the head.

FIG. 23 shows a cross-sectional side view of the anatomic head component 3 which may be used with any of the stem embodiments described herein. The anatomic head component 3 includes a long taper 32 that couples to the corresponding taper in the stem to secure the anatomic head component 3 to the stem. The longer than usual taper (relative to currently-existing systems) allows for a single interface for both anatomic and reverse arthroplasty. Moreover, the long taper 32 extends through the receptacle in the stem and is sized to allow the anatomic head component to be used in the same stem as an inlay articular cup (as described above) without an intermediate tray. The anatomic head component 3 includes a curved, anatomically accurate center and radius curvature of the articular surface 86 that closely matches normal anatomy of the humeral head. The head component 3 includes cutout 87 to reduce the weight of the component. The cutout 87 is disposed between the outer rim of the head 88 and the central tapered protrusion 32. A rounded periphery 89 provides an atraumatic surface when in contact with soft tissue.

Figure 24A:
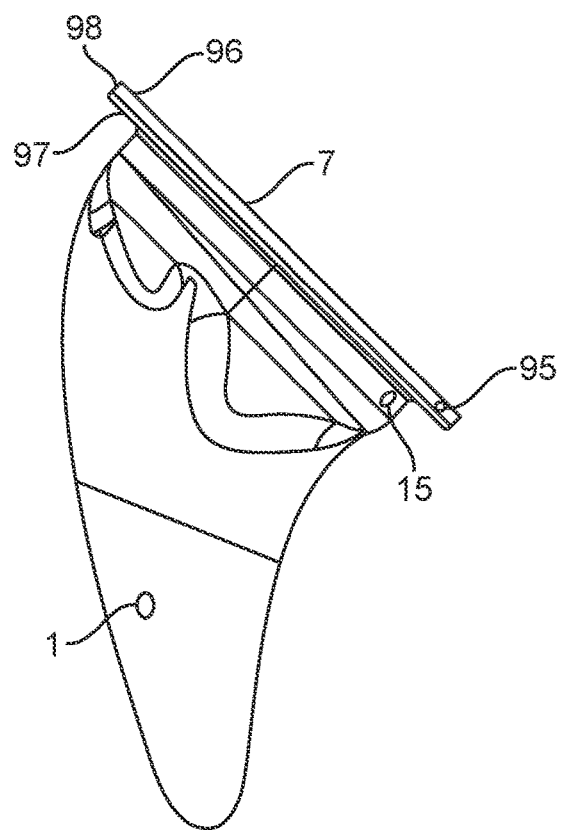
FIG. 24A shows a frontal view of an alternative embodiment of the stem with a collar.
Figure 24B:
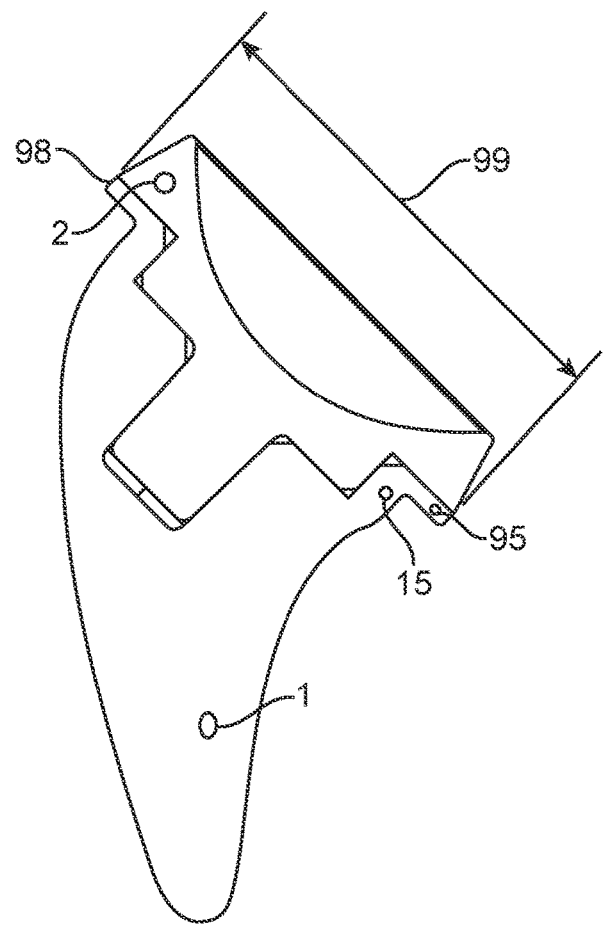
FIG. 24B shows a cross-section of the same embodiment.

FIG. 24A shows a frontal view of an alternative embodiment where the stem has a collar 95 on the cylindrical portion 15 of the stem 1. This embodiment is also known as a "collared" stem and is used with the smallest stem sizes to allow for placement of the head or cup, depending on whether an anatomic or a reverse is being implanted. It is allows the use of the head or cup in a stem that is too small to accommodate them as the larger stems do. The collar 95 has a proximal surface 96, distal surface 97 and radial surface 98. The proximal surface 96 of the collar 95 is congruent to the proximal end 7 of the stem. The distal surface 97 of the collar sits on the resection plane of the humerus. The radial surface 98 has a diameter greater than that of the cylindrical extrusion 15. The mating articular cup 2 component, shown in FIG. 24B, has an outer diameter 99 that is equal to the diameter of the radial surface 98.

Figure 25A:
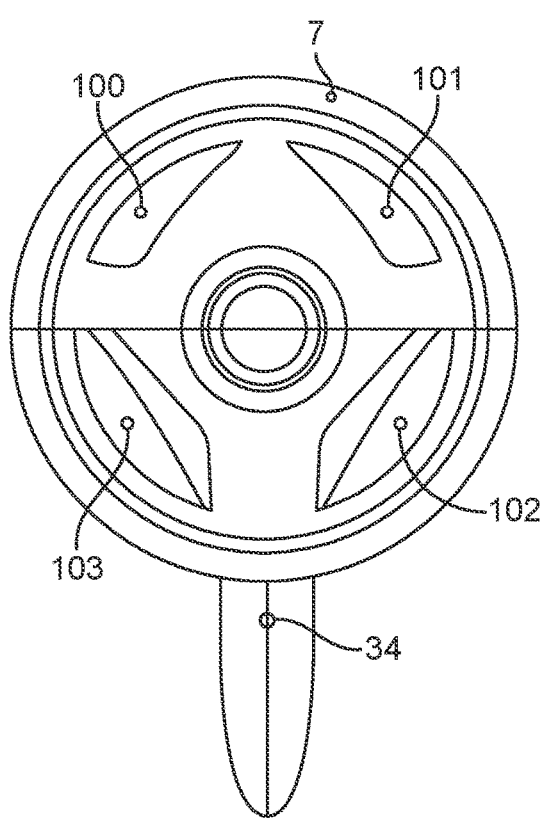
FIG. 25A shows an auxiliary view taken normal to the proximal end of the stem of an alternative embodiment of the stem with fenestrations for implant removal.
Figure 25B:
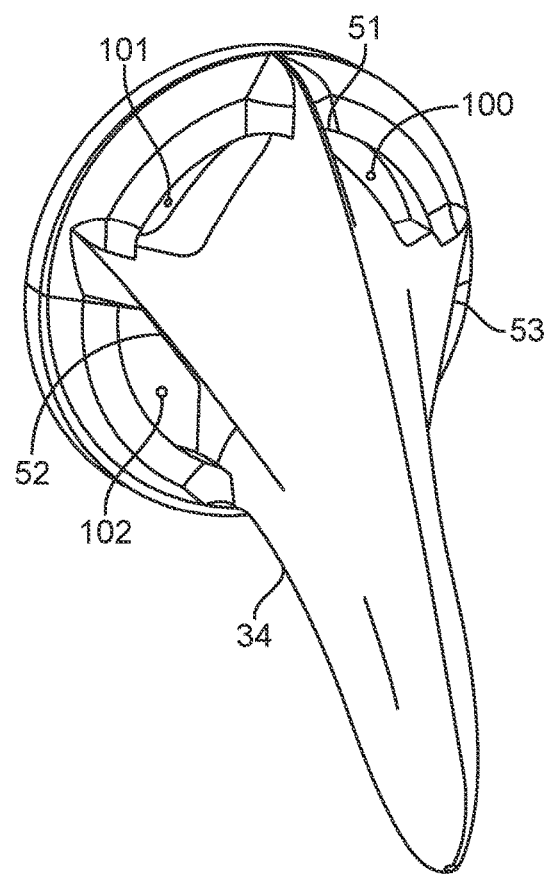
FIG. 25B shows a perspective view of the same embodiment.

FIGS. 25A and 25B shows an alternative embodiment of the stem with fenestrations. The fenestrations are used to insert instruments if the prosthesis needs to be removed. During revision, removal may be made difficult by bone that has grown onto the stem. The fenestrations extend from the proximal end 7 distally. In the embodiment shown in FIG. 23 there are four fenestrations. The first fenestration 100 is located between the lateral fin 51 and the posterior fin 53. A second fenestration 101 is located between the lateral fin 51 and the anterior fin 52. A third fenestration is located between the posterior fin and the medial surface 34. The fourth fenestration 103 is located between the anterior fin and the medial surface. Alternative embodiments may include a different number of fenestrations.

The method to insert the stem is described below. In a first step, the proximal humeral osteotomy 111 is made through the anatomic neck of the humerus. Reference FIG. 27A-27D. The osteotomy can be made using a saw, osteotome or equivalent bone cutting instrument. The osteotomy 111 is a planar cut made at an angle to the long axis 9 of the bone. The osteotomy can be sized using a set of sizing disks 112 and a guide pin 113 placed through the center of the disk 114 to establish the osteotomy center point 115. The set of sizing disks 112 include a matching disk for each implant size. The guide pin 113 also acts as a temporary fixation pin to help hold the disk 112. The disk is a flat cylinder used to visualize the diameter of the proximal portion of the stem relative to the resected bone surface created by the osteotomy 111. At least two slots 116 are cut into the sizing disk 112 to help visualize the extent of the resected bone surface and thereby preventing oversizing of the implant.

Figures 28A, 28B, 28C, 28D:
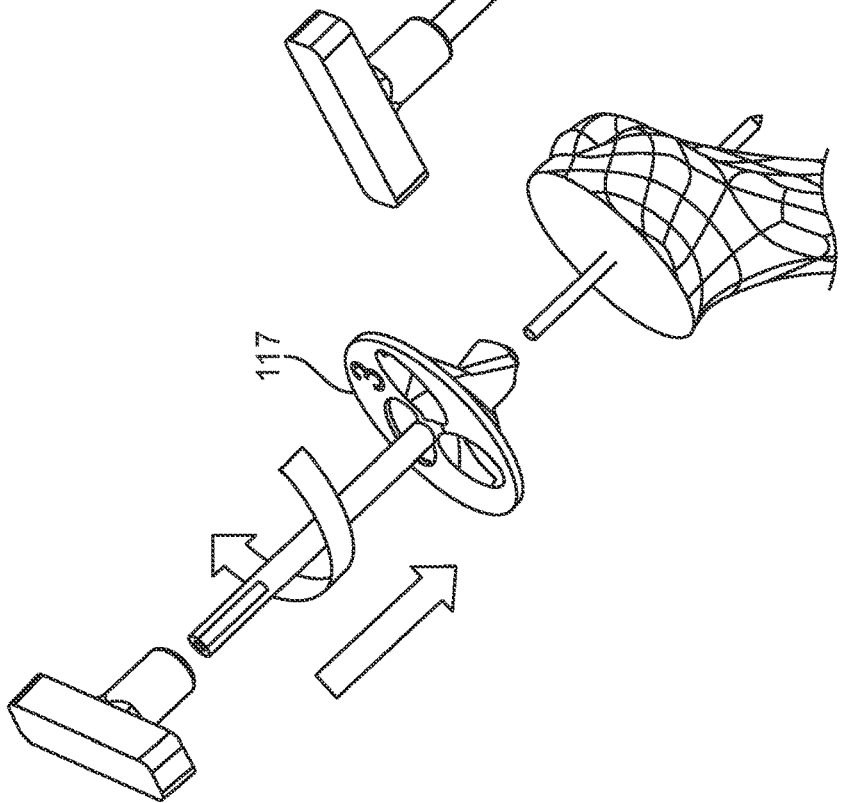
FIG. 28A, 28B, 28C, 28D, 28E, 28F show the reaming procedure to create the proximal bone cavity.
Figure 28F:
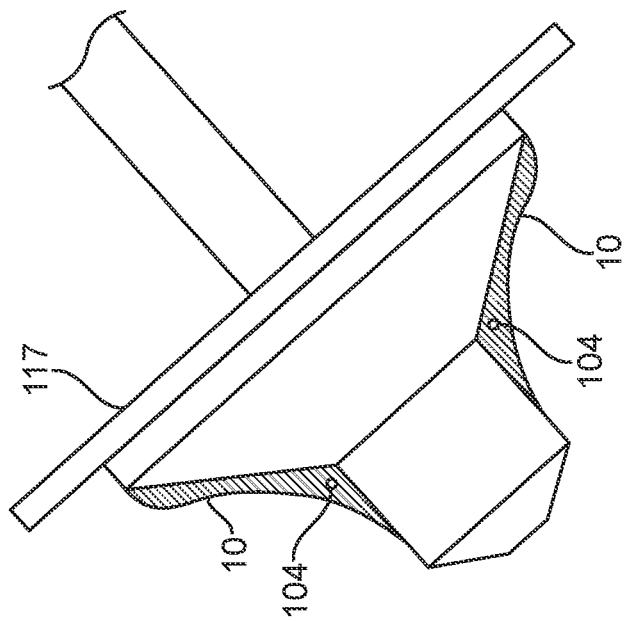
Figure 28E:
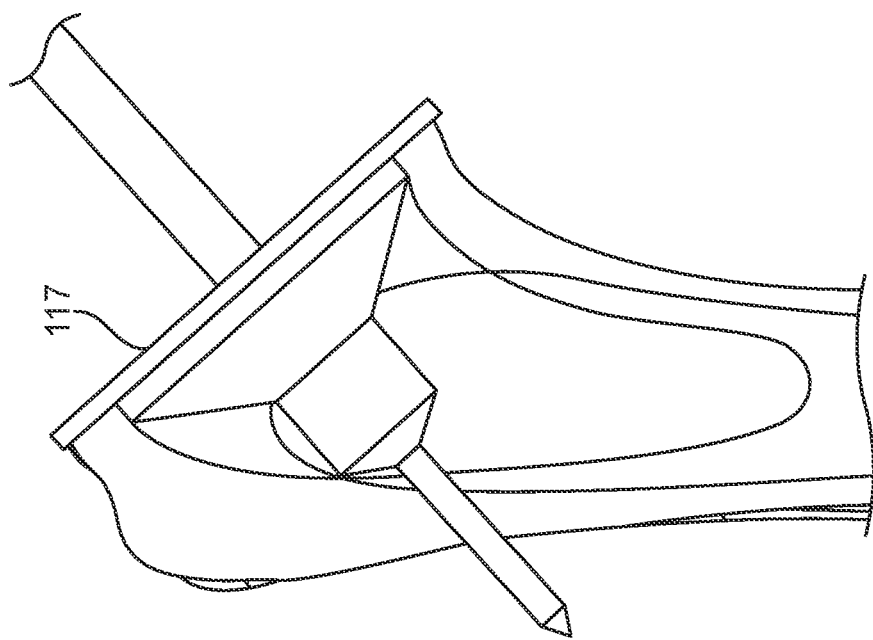

FIG. 28A-28F shows the next step being removal of the proximal bone. The proximal bone of the humerus is removed to accommodate the proximal portion of the final implant. The bone is removed using a proximal reamer 117 that may be attached to handle for manual reaming by hand or a power drill. The humerus is reamed such that the cavity 118 created by the reamer 117 is smaller than the final implant. FIG. 28E shows a cross section of the reamer 117 in the humerus. FIG. 28F shows the reamer over-laid with the outline of the concave taper. The area between the concave taper and the reamer is the volume of bone that will be compacted during the insertion of the stem.

Figure 29:
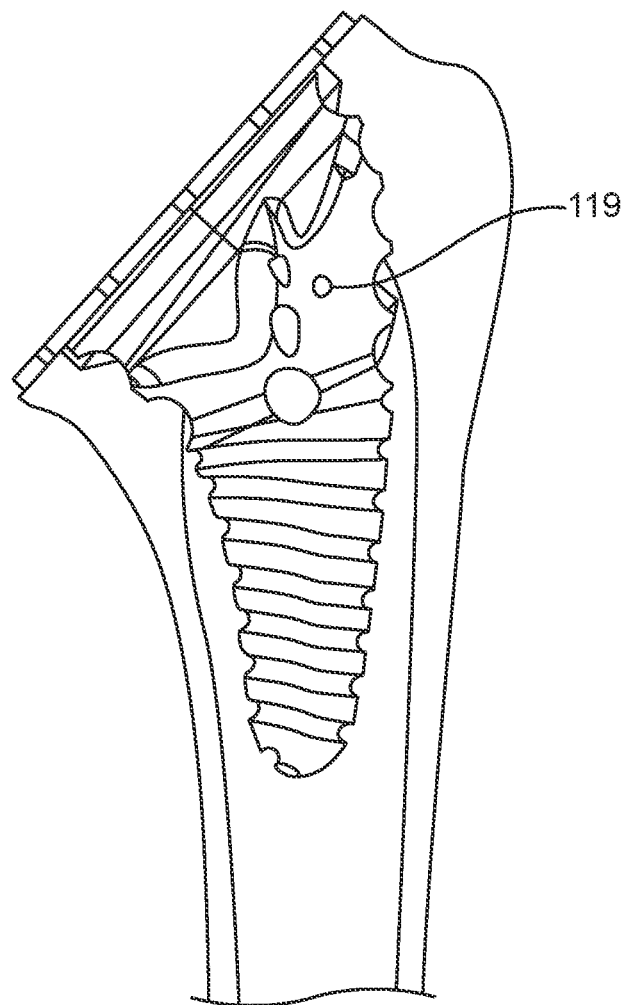
FIG. 29 shows a cross-section of the broach in the humerus.

The following step, shown in FIG. 29, shows a broach 119 that is utilized to compact the bone in the epiphysis and to create space for final implantation of the stem. The stemless broach 119 is designed to minimize bone cutting and improve bone compaction. The broach 119 also serves as the trial for the stem component disclosed herein. The broach may also include slots to visualize the extent of the resected bone relative to broach.

Figure 30A:
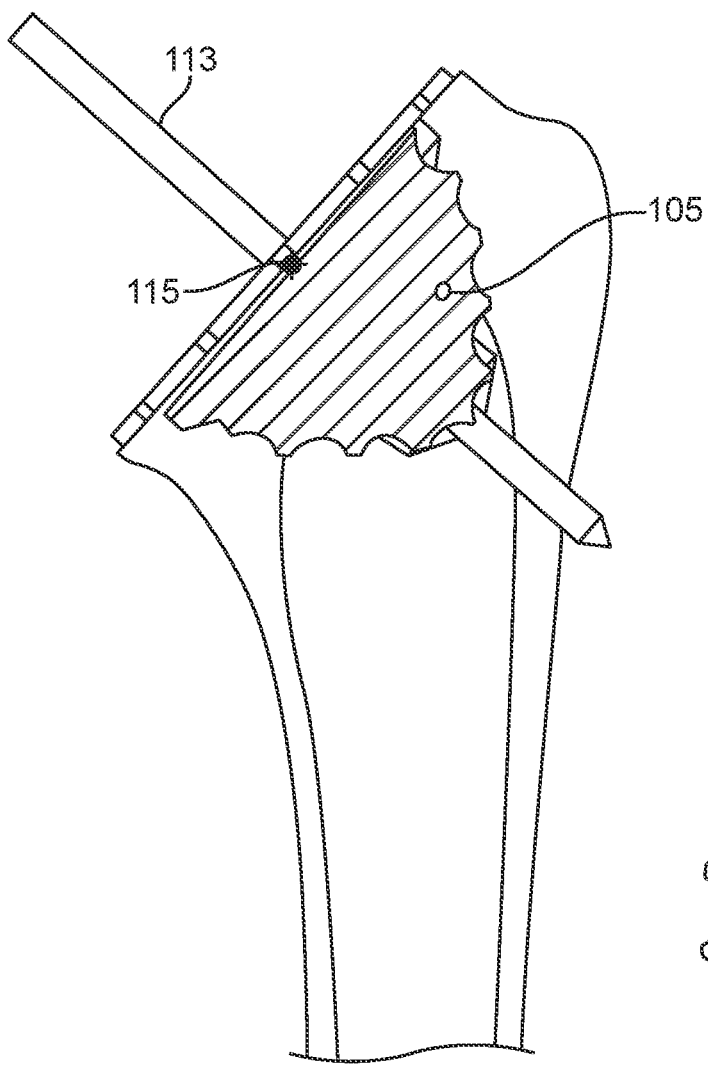
FIG. 30A shows a cross-section of the stemless broach in the humerus.
Figure 30B:
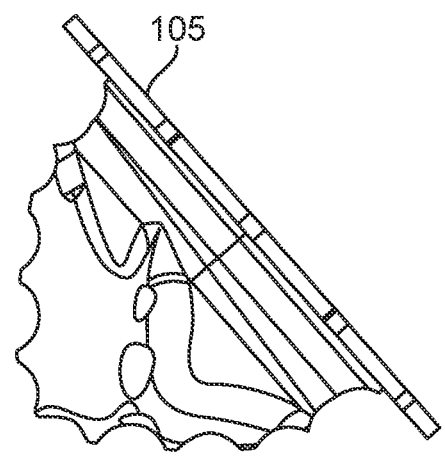
FIG. 30B shows a frontal view of the stemless broach.

FIG. 30A shows an alternative embodiment of the broach where a stemless broach 105 may be used to clear bone proximally. The stemless broach 105 may be inserted over the guide pin 113 to ensure the bone cavity for the stem is located at the osteotomy center point 115. The stemless broach 105, shown also in FIG. 30B, may be used in both 'stemmed' implants and stemless implants. In the process of placing the broach, the metaphyseal bone is compacted, thus achieving additional stability. The stability of the implant is then confirmed. Cementing may optionally be considered if the implant is not satisfactorily stable such as in patients with extremely poor bone quality. Once the glenoid is prepared, the final stem component is fitted with a humeral head or the reversed cup and the joint reduced.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub-combination or a variation of a sub combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A shoulder arthroplasty implant comprising:
a stem having a proximal portion, a distal portion, an anterior portion, a posterior portion, a medial portion, and a lateral portion, wherein the stem has a size and shape for insertion into an intramedullary canal of the humerus bone, the humerus having a metaphysis and a diaphysis, wherein the proximal portion comprises a cylindrical rim defining a face that is configured to sit flush with respect to the resection plane, wherein the proximal portion of the stem comprises a proximal taper having a generally conical shape that is centered with respect to a central axis of the cylindrical rim, the proximal taper decreasing in size in a direction extending from the proximal portion toward the distal portion, wherein the distal portion comprises a distal taper decreasing in size in a direction extending from the proximal portion toward the distal portion, wherein the distal taper comprises at least a first taper in a direction extending between the medial portion and the lateral portion, the first taper comprising a convex lateral curve that extends from a most lateral edge of the cylindrical rim toward a distal end of the stem, and the first taper comprising a concave medial curve that extends from a most medial edge of the cylindrical rim toward the distal end of the stem, wherein the first taper is curved such that the distal end of the stem is offset laterally with respect to the central axis of the cylindrical rim, wherein an anterior-posterior width at the distal portion is less than a medial-lateral width at the distal portion, and wherein the shape of the stem is configured to load the metaphysis with a load greater than a load on the diaphysis.

2. The system of claim 1, wherein the implant further comprises a lateral fin, an anterior fin, and a posterior fin, wherein the lateral fin extends radially outward from the lateral portion of the stem, the anterior fin extends radially outward from the anterior portion of the stem, and the posterior fin extends radially outward from the posterior portion of the stem, and wherein the lateral, anterior, and posterior fins are configured to engage cancellous bone in the metaphysis or epiphysis to provide rotational stability to the stem.

3. The system of claim 1,
wherein a first point is disposed on an anterior portion of cylindrical rim and a second point is disposed on a posterior portion of the cylindrical rim, and
wherein a third point is disposed distally away from the first point and the third point is disposed on an anterior portion of the distal taper, and
wherein a fourth point is disposed distally away from the second point and the fourth point is disposed on a posterior portion of the distal taper, and
wherein the first, second, third, and fourth points define a first total included angle of a proximal portion of the distal taper, and
wherein a fifth point is disposed at a distal end of the stem and disposed on the anterior portion of the stem, and
wherein a sixth point is disposed at the distal end of the stem and disposed on the posterior portion of stem, and
wherein the third, fourth, fifth, and sixth points define a second total included angle of a distal portion of the distal taper, and
wherein the second total included angle is less than the first total included angle.

4. The system of claim 1, wherein a distal portion of the stem comprises an hourglass shaped cross-section with a width extending in a direction from the anterior portion toward the posterior portion at the medial portion or at the lateral portion is greater than a width extending in the direction from the anterior portion toward the posterior portion at a center of the cross-section.

5. The system of claim 1, wherein a distal portion of the stem comprises a cutout section extending through the stem in a direction from the anterior portion toward the posterior portion, and wherein the cutout comprises medial and lateral edges which are offset from a medial surface and a lateral surface of the stem, and wherein the cutout is configured to carry bone graft material.

6. The system of claim 1, wherein the cylindrical rim comprises one or more protrusions extending outward therefrom, the one or more protrusions configured to be received into a corresponding receptacle in an articular cup or a head component.

7. The system of claim 1, further comprising a collar element disposed circumferentially around the proximal portion of the stem.

8. The system of claim 1, further comprising one or more fenestrations disposed in the proximal portion of the stem, the one or more fenestrations extending in a direction from the proximal portion toward the distal portion, wherein the one or more fenestrations are sized to allow a surgical instrument to pass therethrough.

9. The system of claim 1, wherein the articular cup is coupled directly to the stem.

10. The system of claim 1, wherein the stem further comprises a tapered receptacle disposed in the proximal portion of the stem, the tapered receptacle configured to receive a cooperating tapered protrusion disposed on the articular cup.

11. The system of claim 1, further comprising a coating disposed over at least a portion of the stem, the coating configured to promote bone ingrowth into the stem.

12. The system of claim 1, wherein the stem is a monolithic piece.

13. A shoulder arthroplasty system comprising:
an implant; and
an articular cup coupled to the implant, the articular cup including an articular surface with an apex, the apex being configured to be disposed distal to a resection plane in a humerus bone;
the implant including:
a stem having a proximal portion, a distal portion, an anterior portion, a posterior portion, a medial portion, and a lateral portion, wherein the stem has a size and shape for insertion into an intramedullary canal of the humerus bone, the humerus having a metaphysis and a diaphysis, wherein the proximal portion comprises a cylindrical rim defining a face that is configured to sit flush with respect to the resection plane,
wherein the proximal portion of the stem comprises a proximal taper having a generally conical shape that is centered with respect to a central axis of the cylindrical rim, the proximal taper decreasing in size in a direction extending from the proximal portion toward the distal portion,
wherein the distal portion comprises a distal taper in which a width of the stem in a direction extending between the medial portion and the lateral portion decreases in size in a direction extending from the proximal portion toward the distal portion, the distal taper comprising a convex lateral curve that extends from a most lateral edge of the cylindrical rim toward a distal end of the stem, and the distal taper comprising a concave medial curve that extends from a most medial edge of the cylindrical rim toward the distal end of the stem, wherein the distal taper is curved such that the distal end of the stem is offset laterally with respect to the central axis of the cylindrical rim, and wherein the shape of the stem is configured to apply a first load to the metaphysis portion of the humerus bone and apply a second load to the diaphysis portion of the humerus bone, the first load being greater than the second load.

\* \* \* \* \*